US012672958B2

(12) United States Patent
Yohanan et al.

(10) Patent No.: US 12,672,958 B2
(45) Date of Patent: Jul. 7, 2026

(54) SEALING MEMBER FOR PROSTHETIC HEART VALVE

(71) Applicant: Edwards Lifesciences Corporation, Irvine, CA (US)

(72) Inventors: Ziv Yohanan, Kfar Hahoresh (IL); Tamir S. Levi, Zikhron Yaakov (IL); David Maimon, Atlit (IL); Michael G. Valdez, Riverside, CA (US); Tram Ngoc Nguyen, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1116 days.

(21) Appl. No.: 17/502,018

(22) Filed: Oct. 14, 2021

(65) Prior Publication Data

US 2022/0031453 A1 Feb. 3, 2022

Related U.S. Application Data

(62) Division of application No. 16/121,947, filed on Sep. 5, 2018, now Pat. No. 11,147,667.

(Continued)

(51) Int. Cl.
*A61F 2/24* (2006.01)

(52) U.S. Cl.
CPC .......... *A61F 2/2418* (2013.01); *A61F 2/2433* (2013.01); *A61F 2/2436* (2013.01); *A61F 2/246* (2013.01); *A61F 2220/0016* (2013.01); *A61F 2220/005* (2013.01); *A61F 2220/0075* (2013.01); *A61F 2250/0039* (2013.01); *A61F 2250/006* (2013.01); *A61F 2250/0069* (2013.01)

(58) Field of Classification Search
CPC ........................ A61F 2250/006; A61F 2/2618
See application file for complete search history.

(56) References Cited

U.S. PATENT DOCUMENTS

| | | | |
|---|---|---|---|
| 30,912 | A | 12/1860 | Hancock |
| 3,409,013 | A | 11/1968 | Berry |
| | | (Continued) | |

FOREIGN PATENT DOCUMENTS

| | | |
|---|---|---|
| DE | 0144167 C | 9/1903 |
| DE | 2246526 A1 | 3/1973 |
| | (Continued) | |

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

(Continued)

*Primary Examiner* — Alvin J Stewart
(74) *Attorney, Agent, or Firm* — Klarquist Sparkman LLP

(57) ABSTRACT

An implantable prosthetic valve can include an annular frame comprising an inflow end and an outflow end and being radially collapsible and expandable between a radially collapsed configuration and a radially expanded configuration. A leaflet structure can be positioned within the frame and secured thereto. An outer skirt can be positioned around an outer surface of the frame and secured to the frame and an annular sealing member can be positioned around an outer surface of the outer skirt and secured to the outer skirt.

18 Claims, 19 Drawing Sheets

Related U.S. Application Data

(60) Provisional application No. 62/556,219, filed on Sep. 8, 2017.

(56) References Cited

U.S. PATENT DOCUMENTS

| | | | |
|---|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Ende et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eldenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |

(56)        References Cited

U.S. PATENT DOCUMENTS

| | | | |
|---|---|---|---|
| 7,510,575 B2 | 3/2009 | Spenser et al. | |
| 7,563,280 B2 | 7/2009 | Anderson et al. | |
| 7,585,321 B2 | 9/2009 | Cribier | |
| 7,618,446 B2 | 11/2009 | Andersen et al. | |
| 7,618,447 B2 | 11/2009 | Case et al. | |
| 7,655,034 B2 | 2/2010 | Mitchell et al. | |
| 7,785,366 B2 | 8/2010 | Maurer et al. | |
| 7,959,665 B2 | 6/2011 | Pienknagura | |
| 7,959,672 B2 | 6/2011 | Salahieh et al. | |
| 7,993,394 B2 | 8/2011 | Hariton et al. | |
| 8,029,556 B2 | 10/2011 | Rowe | |
| 8,075,611 B2 | 12/2011 | Millwee et al. | |
| 8,128,686 B2 | 3/2012 | Paul, Jr. et al. | |
| 8,167,932 B2 | 5/2012 | Bourang et al. | |
| 8,291,570 B2 | 10/2012 | Eldenschink et al. | |
| 8,348,998 B2 | 1/2013 | Pintor et al. | |
| 8,449,606 B2 | 5/2013 | Eliasen et al. | |
| 8,454,685 B2 | 6/2013 | Hariton et al. | |
| 8,652,203 B2 | 2/2014 | Quadri et al. | |
| 8,747,463 B2 | 6/2014 | Fogarty et al. | |
| 8,821,569 B2 * | 9/2014 | Gurskis | A61F 2/2439 |
| | | | 623/2.11 |
| 9,078,781 B2 | 7/2015 | Ryan et al. | |
| 9,216,076 B2 * | 12/2015 | Mitra | A61L 31/048 |
| 9,370,418 B2 * | 6/2016 | Pintor | A61F 2/2418 |
| 9,636,222 B2 * | 5/2017 | Oslund | A61F 2/2418 |
| 9,675,451 B2 * | 6/2017 | Garde | A61F 2/2409 |
| 9,848,981 B2 * | 12/2017 | Suri | A61F 2/2418 |
| 9,974,650 B2 * | 5/2018 | Nguyen-Thien-Nhon | |
| | | | A61F 2/2418 |
| 10,179,043 B2 * | 1/2019 | Cohen-Tzemach | |
| | | | A61F 2/2418 |
| 10,195,025 B2 * | 2/2019 | Levi | A61F 2/2427 |
| 10,258,464 B2 * | 4/2019 | Delaloye | A61F 2/2469 |
| 10,314,698 B2 * | 6/2019 | Skemp | A61F 2/2409 |
| 10,413,401 B2 * | 9/2019 | Eberhardt | A61F 2/2409 |
| 11,207,176 B2 * | 12/2021 | Delaloye | A61F 2/2418 |
| 11,504,231 B2 * | 11/2022 | Carlino | A61F 2/2409 |
| 11,654,023 B2 * | 5/2023 | Zamani | A61F 2/2418 |
| | | | 623/2.11 |
| 11,759,317 B2 * | 9/2023 | Nguyen | D03D 15/283 |
| | | | 623/2.37 |
| 12,036,112 B2 * | 7/2024 | Braido | A61F 2/2433 |
| 12,193,933 B2 * | 1/2025 | Zamani | A61F 2/2412 |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0055774 A1 * | 5/2002 | Liddicoat | A61F 2/2409 |
| | | | 623/2.38 |
| 2002/0138135 A1 | 9/2002 | Duerig et al. | |
| 2002/0143390 A1 | 10/2002 | Ishii | |
| 2002/0173842 A1 | 11/2002 | Buchanan | |
| 2003/0014105 A1 | 1/2003 | Cao | |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2004/0024452 A1 | 2/2004 | Kruse et al. | |
| 2004/0039436 A1 | 2/2004 | Spenser et al. | |
| 2004/0078074 A1 | 4/2004 | Anderson et al. | |
| 2004/0186558 A1 | 9/2004 | Pavcnik et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0010285 A1 | 1/2005 | Lambrecht et al. | |
| 2005/0075725 A1 | 4/2005 | Rowe | |
| 2005/0075728 A1 | 4/2005 | Nguyen et al. | |
| 2005/0096736 A1 | 5/2005 | Osse et al. | |
| 2005/0096738 A1 | 5/2005 | Cali et al. | |
| 2005/0188525 A1 | 9/2005 | Weber et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0004442 A1 * | 1/2006 | Spenser | A61F 2/2472 |
| | | | 623/1.21 |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0108090 A1 | 5/2006 | Ederer et al. | |
| 2006/0149350 A1 | 7/2006 | Patel et al. | |
| 2006/0183383 A1 | 8/2006 | Asmus et al. | |
| 2006/0195184 A1 | 8/2006 | Lane et al. | |
| 2006/0229719 A1 | 10/2006 | Marquez et al. | |
| 2006/0259136 A1 | 11/2006 | Nguyen et al. | |
| 2006/0259137 A1 | 11/2006 | Artof et al. | |
| 2006/0287717 A1 | 12/2006 | Rowe et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0112422 A1 | 5/2007 | Dehdashtian | |
| 2007/0162102 A1 | 7/2007 | Ryan et al. | |
| 2007/0203503 A1 | 8/2007 | Salahieh et al. | |
| 2007/0203575 A1 | 8/2007 | Forster et al. | |
| 2007/0203576 A1 | 8/2007 | Lee et al. | |
| 2007/0208550 A1 | 9/2007 | Cao et al. | |
| 2007/0213813 A1 | 9/2007 | Von Segesser et al. | |
| 2007/0233228 A1 | 10/2007 | Eberhardt et al. | |
| 2007/0239265 A1 * | 10/2007 | Birdsall | A61L 27/303 |
| | | | 623/2.11 |
| 2007/0260305 A1 | 11/2007 | Drews et al. | |
| 2007/0265700 A1 | 11/2007 | Eliasen et al. | |
| 2007/0270944 A1 * | 11/2007 | Bergheim | A61L 27/3882 |
| | | | 623/2.18 |
| 2008/0021546 A1 | 1/2008 | Patz et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0183271 A1 | 7/2008 | Frawley et al. | |
| 2008/0208327 A1 | 8/2008 | Rowe | |
| 2008/0243245 A1 | 10/2008 | Thambar et al. | |
| 2008/0255660 A1 | 10/2008 | Guyenot et al. | |
| 2008/0275537 A1 | 11/2008 | Limon | |
| 2008/0294248 A1 | 11/2008 | Yang et al. | |
| 2009/0099653 A1 * | 4/2009 | Suri | A61F 2/2418 |
| | | | 623/2.11 |
| 2009/0112311 A1 * | 4/2009 | Miles | A61F 2/246 |
| | | | 623/2.38 |
| 2009/0118826 A1 | 5/2009 | Khaghani | |
| 2009/0125118 A1 | 5/2009 | Gong | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0287296 A1 | 11/2009 | Manasse | |
| 2009/0287299 A1 | 11/2009 | Tabor et al. | |
| 2009/0299452 A1 | 12/2009 | Eidenschink et al. | |
| 2009/0319037 A1 | 12/2009 | Rowe et al. | |
| 2010/0049313 A1 | 2/2010 | Alon et al. | |
| 2010/0082094 A1 | 4/2010 | Quadri et al. | |
| 2010/0168844 A1 * | 7/2010 | Toomes | A61F 2/2418 |
| | | | 623/2.18 |
| 2010/0185277 A1 | 7/2010 | Braido et al. | |
| 2010/0198347 A1 | 8/2010 | Zakay et al. | |
| 2010/0204781 A1 | 8/2010 | Alkhatib | |
| 2011/0004299 A1 | 1/2011 | Essinger et al. | |
| 2011/0015729 A1 | 1/2011 | Jimenez et al. | |
| 2011/0022157 A1 | 1/2011 | Essinger et al. | |
| 2011/0066224 A1 | 3/2011 | White | |
| 2011/0098802 A1 * | 4/2011 | Braido | A61F 2/243 |
| | | | 623/2.11 |
| 2011/0137397 A1 | 6/2011 | Chau et al. | |
| 2011/0218619 A1 | 9/2011 | Benichou et al. | |
| 2011/0319991 A1 | 12/2011 | Hariton et al. | |
| 2012/0022629 A1 * | 1/2012 | Perera | C08L 63/00 |
| | | | 623/1.11 |
| 2012/0089223 A1 | 4/2012 | Nguyen et al. | |
| 2012/0101571 A1 | 4/2012 | Thambar et al. | |
| 2012/0123529 A1 | 5/2012 | Levi et al. | |
| 2012/0259409 A1 | 10/2012 | Nguyen et al. | |
| 2013/0018458 A1 * | 1/2013 | Yohanan | A61F 2/2418 |
| | | | 623/2.38 |

(56)　　　　　References Cited

U.S. PATENT DOCUMENTS

| | | | |
|---|---|---|---|
| 2013/0023985 A1 | 1/2013 | Khairkhahan et al. | |
| 2013/0046373 A1 | 2/2013 | Cartledge et al. | |
| 2013/0150956 A1 | 6/2013 | Yohanan et al. | |
| 2013/0166017 A1 | 6/2013 | Cartledge et al. | |
| 2013/0190857 A1 | 7/2013 | Mitra et al. | |
| 2013/0190862 A1 | 7/2013 | Pintor et al. | |
| 2013/0274873 A1 | 10/2013 | Delaloye et al. | |
| 2013/0304200 A1* | 11/2013 | McLean | A61F 2/2418 |
| | | | 623/2.18 |
| 2013/0310926 A1 | 11/2013 | Hariton | |
| 2013/0317598 A1 | 11/2013 | Rowe et al. | |
| 2013/0331929 A1* | 12/2013 | Mitra | A61F 2/2418 |
| | | | 623/2.11 |
| 2014/0194981 A1 | 7/2014 | Menk et al. | |
| 2014/0200661 A1 | 7/2014 | Pintor et al. | |
| 2014/0209238 A1 | 7/2014 | Bonyuet et al. | |
| 2014/0222136 A1 | 8/2014 | Geist et al. | |
| 2014/0243966 A1* | 8/2014 | Garde | A61F 2/2418 |
| | | | 623/2.18 |
| 2014/0243969 A1* | 8/2014 | Venkatasubramanian | |
| | | | A61F 2/2418 |
| | | | 623/2.38 |
| 2014/0277388 A1* | 9/2014 | Skemp | A61F 2/2418 |
| | | | 623/2.37 |
| 2014/0277412 A1* | 9/2014 | Bortlein | A61F 2/2418 |
| | | | 623/2.11 |
| 2014/0277417 A1* | 9/2014 | Schraut | A61F 2/2418 |
| | | | 623/2.17 |
| 2014/0277419 A1* | 9/2014 | Garde | A61F 2/2403 |
| | | | 623/2.18 |
| 2014/0277424 A1* | 9/2014 | Oslund | A61F 2/2436 |
| | | | 623/2.38 |
| 2014/0277426 A1* | 9/2014 | Dakin | A61F 2/246 |
| | | | 623/2.38 |
| 2014/0277428 A1* | 9/2014 | Skemp | A61F 2/2418 |
| | | | 623/2.42 |
| 2014/0277563 A1 | 9/2014 | White | |
| 2014/0296962 A1 | 10/2014 | Cartledge et al. | |
| 2014/0330372 A1 | 11/2014 | Weston et al. | |
| 2014/0343670 A1 | 11/2014 | Bakis et al. | |
| 2014/0343671 A1 | 11/2014 | Yohanan et al. | |
| 2014/0350667 A1 | 11/2014 | Braido et al. | |
| 2014/0350668 A1* | 11/2014 | Delaloye | A61F 2/2418 |
| | | | 623/2.17 |
| 2015/0073544 A1* | 3/2015 | Gorman, III | A61L 31/10 |
| | | | 623/2.18 |
| 2015/0073545 A1 | 3/2015 | Braido | |
| 2015/0073546 A1 | 3/2015 | Braido | |
| 2015/0122687 A1* | 5/2015 | Zeng | A61B 50/30 |
| | | | 53/467 |
| 2015/0135506 A1 | 5/2015 | White | |
| 2015/0157455 A1 | 6/2015 | Hoang et al. | |
| 2015/0190227 A1* | 7/2015 | Johnson | A61F 2/2409 |
| | | | 623/2.38 |
| 2015/0209136 A1* | 7/2015 | Braido | A61F 2/2418 |
| | | | 623/2.18 |
| 2015/0209141 A1* | 7/2015 | Braido | A61F 2/2418 |
| | | | 623/2.17 |
| 2015/0216658 A1* | 8/2015 | Braido | A61F 2/2409 |
| | | | 623/2.13 |
| 2015/0327995 A1* | 11/2015 | Morin | A61F 2/2418 |
| | | | 623/2.17 |
| 2015/0327996 A1* | 11/2015 | Fahim | A61F 2/2418 |
| | | | 623/2.17 |
| 2016/0030165 A1* | 2/2016 | Mitra | A61F 2/0095 |
| | | | 206/438 |
| 2016/0143732 A1* | 5/2016 | Glimsdale | A61F 2/2418 |
| | | | 29/525.09 |
| 2016/0194425 A1* | 7/2016 | Mitra | C08F 220/56 |
| | | | 524/56 |
| 2016/0235531 A1* | 8/2016 | Ciobanu | A61F 2/2427 |
| 2016/0317305 A1* | 11/2016 | Pelled | A61F 2/2412 |
| 2016/0324631 A1 | 11/2016 | Lane et al. | |

| | | | |
|---|---|---|---|
| 2016/0354201 A1* | 12/2016 | Keogh | A61F 2/2418 |
| 2016/0361160 A1* | 12/2016 | Braido | A61F 2/2418 |
| 2017/0014229 A1 | 1/2017 | Nguyen-Thien-Nhon et al. | |
| 2017/0172739 A1 | 6/2017 | Chang et al. | |
| 2017/0189174 A1* | 7/2017 | Braido | A61F 2/2436 |
| 2017/0273786 A1* | 9/2017 | Weber | A61F 2/2418 |
| 2017/0281337 A1* | 10/2017 | Campbell | A61F 2/2409 |
| 2018/0028310 A1 | 2/2018 | Gurovich et al. | |
| 2018/0153689 A1 | 6/2018 | Maimon et al. | |
| 2018/0168804 A1* | 6/2018 | Nguyen | A61F 2/2409 |
| 2018/0206982 A1* | 7/2018 | Haivatov | A61F 2/2418 |
| 2018/0325665 A1 | 11/2018 | Gurovich et al. | |
| 2018/0344456 A1 | 12/2018 | Barash et al. | |
| 2019/0053895 A1* | 2/2019 | Levi | A61F 2/2415 |
| 2019/0053899 A1* | 2/2019 | Levi | A61F 2/2418 |
| 2019/0076244 A1* | 3/2019 | Yohanan | A61F 2/2418 |
| 2019/0091014 A1* | 3/2019 | Arcaro | A61F 2/2433 |
| 2019/0099265 A1* | 4/2019 | Braido | A61F 2/86 |
| 2019/0374326 A1* | 12/2019 | Mitra | A61F 2/2418 |
| 2020/0000586 A1* | 1/2020 | Tian | A61F 2/2445 |
| 2020/0085573 A1* | 3/2020 | Armer | A61F 2/2457 |
| 2020/0121454 A1* | 4/2020 | Spence | A61F 2/2454 |
| 2020/0337837 A1* | 10/2020 | Mitra | A61F 2/2433 |
| 2022/0183831 A1* | 6/2022 | Burkart | A61F 2/2418 |
| 2022/0226115 A1* | 7/2022 | Le | A61F 2/9522 |
| 2023/0017301 A1* | 1/2023 | Sherman | A61F 2/2418 |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 2898858 A1 | 7/2015 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 0018333 A1 | 4/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005055883 A1 | 6/2005 |
| WO | 2005084595 A1 | 9/2005 |
| WO | WO-2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |

(56)  References Cited

FOREIGN PATENT DOCUMENTS

| WO | 2006138173 | A2 | 12/2006 |
|----|-----------|-----|---------|
| WO | 2005102015 | A3 | 4/2007 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |
| WO | 2017011697 | A1 | 1/2017 |
| WO | WO-2019144036 | A1 | 7/2019 |

OTHER PUBLICATIONS

Bailey, S. "Percutaneous Expandable Prosthetic Valves," Textbook of Interventional Cardiology vol. 2, 2nd Ed. pp. 1268-1276. 1994.

H.R. Andersen "History of Percutaneous Aortic Valve Prosthesis," Herz No. 34. pp. 343-346. 2009.

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Uchida, "Modifications of Gianturco Expandable Wire Stents," American Journal of Roentgenology, vol. 150. pp. 1185-1187. 1986.

Wheatley, "Valve Prostheses," Operative Surgery, 4th ed. pp. 415-424. 1986.

* cited by examiner

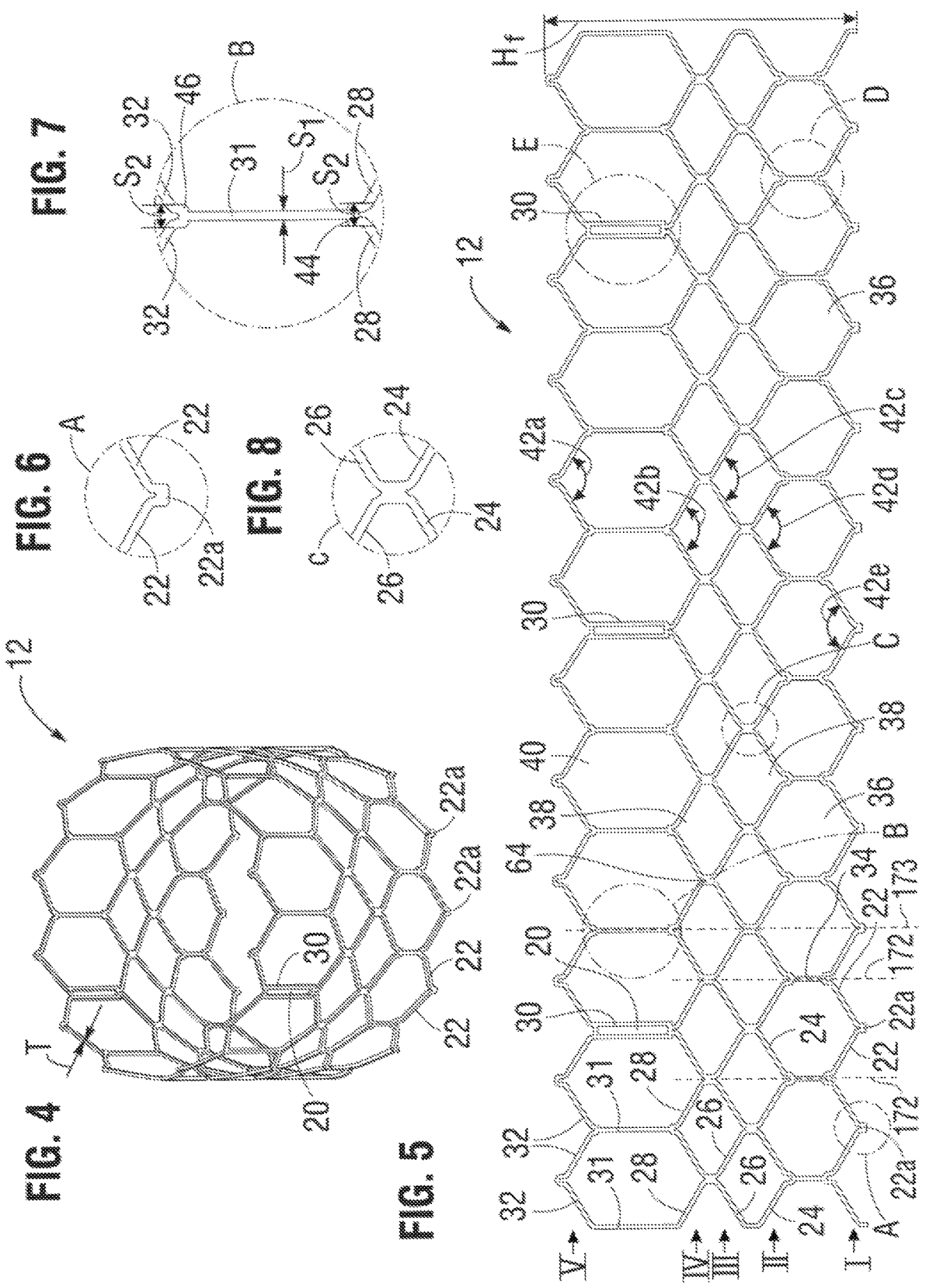

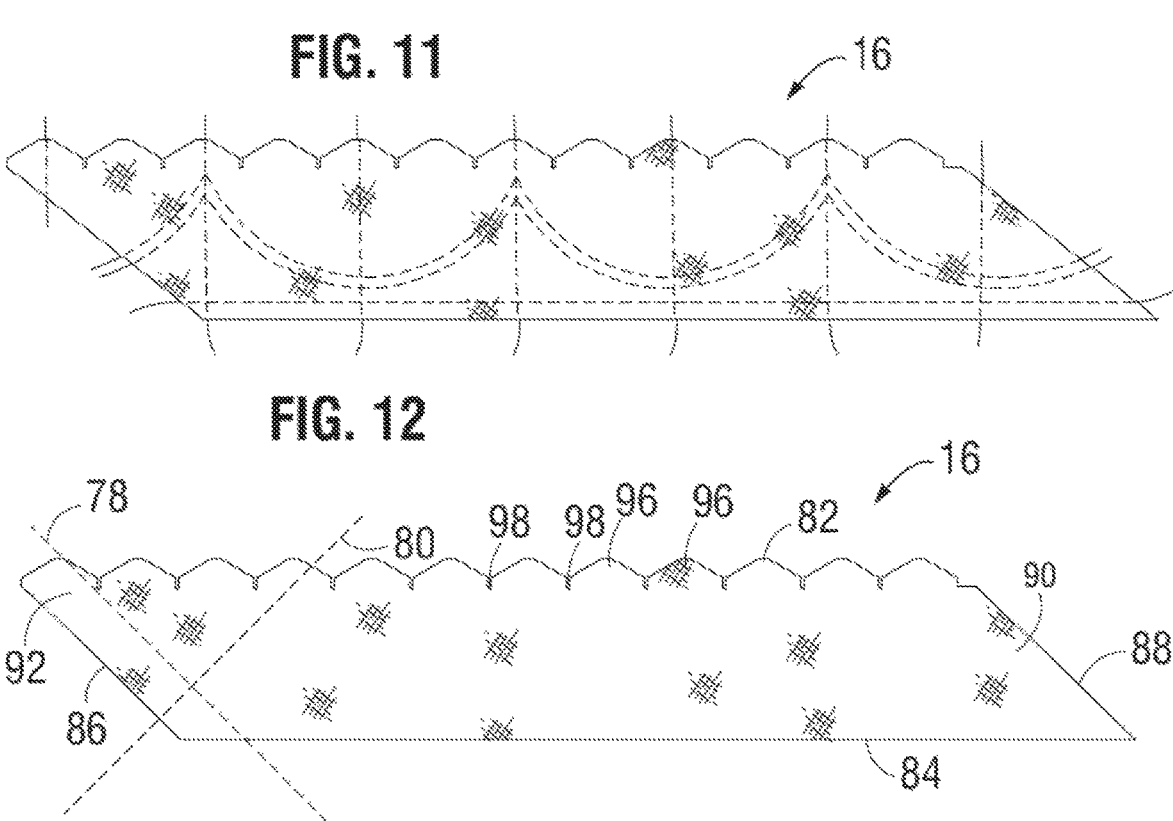
FIG. 11
FIG. 12
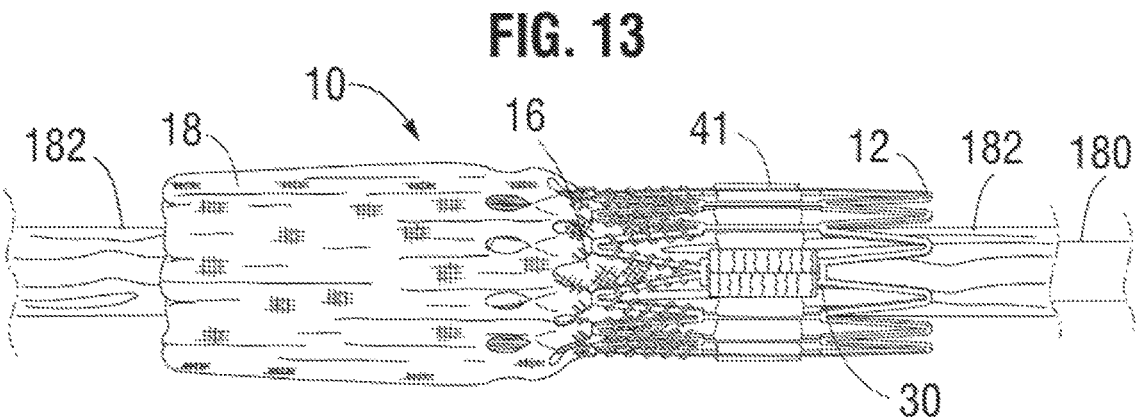
FIG. 13

FIG. 14
FIG. 15
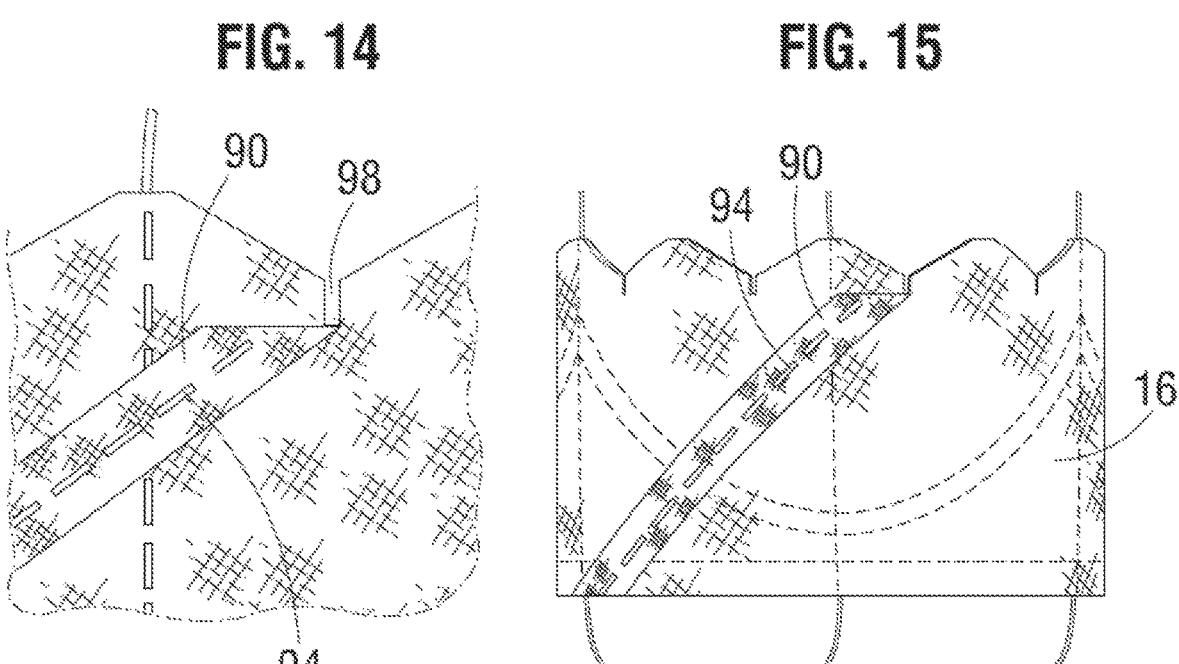
FIG. 16
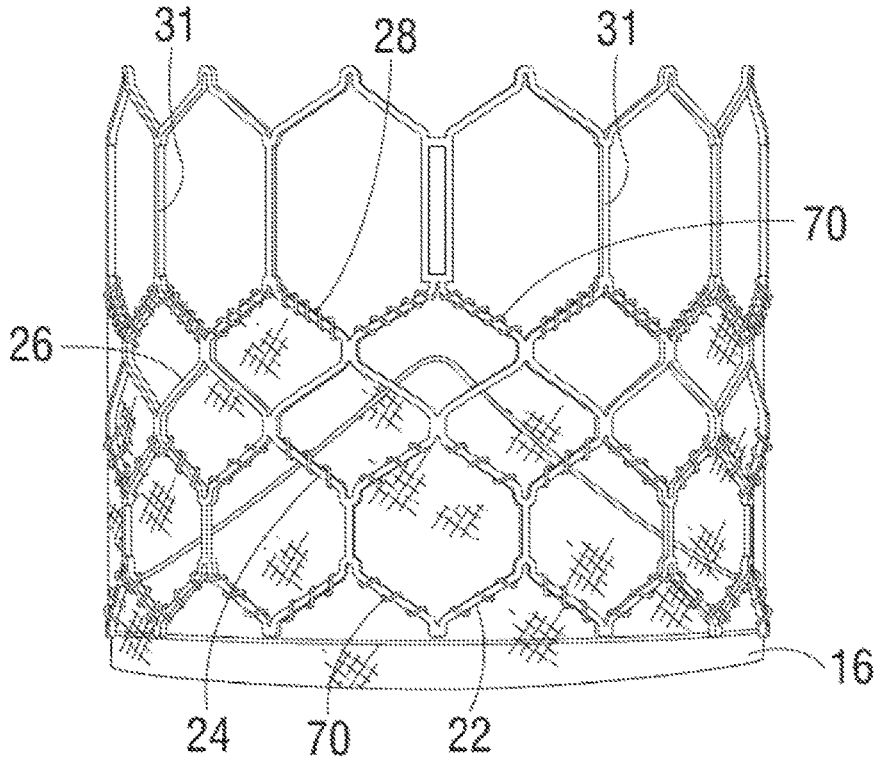

SEALING MEMBER FOR PROSTHETIC HEART VALVE

CROSS REFERENCE TO RELATED APPLICATION

This application is a divisional of U.S. patent application Ser. No. 16/121,947, filed Sep. 5, 2018, which claims the benefit of U.S. Provisional Application No. 62/556,219, filed Sep. 8, 2017, which are incorporated by reference herein in their entireties.

FIELD

The present disclosure relates to implantable, expandable prosthetic devices and to methods and apparatuses for such prosthetic devices.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans. Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For example, collapsible transcatheter prosthetic heart valves can be crimped to a compressed state and percutaneously introduced in the compressed state on a catheter and expanded to a functional size at the desired position by balloon inflation or by utilization of a self-expanding frame or stent.

A prosthetic valve for use in such a procedure can include a radially collapsible and expandable frame to which leaflets of the prosthetic valve can be coupled. For example, U.S. Pat. Nos. 6,730,118, 7,393,360, 7,510,575, 7,993,394, and 9,393,110, which are incorporated herein by reference in their entirety, describe exemplary collapsible and expandable transcatheter prosthetic heart valves.

The prosthetic valve can be percutaneously introduced in a collapsed configuration on a catheter and expanded in the desired position by balloon inflation, mechanical expansion, or by utilization of a self-expanding frame or stent. A challenge in catheter-implanted prosthetic valves is control of perivalvular leakage around the valve, which can occur for a period of time following initial implantation. An additional challenge includes the process of crimping such a prosthetic valve to a profile suitable for percutaneous delivery to a patient.

SUMMARY

Embodiments of a radially collapsible and expandable prosthetic valve are disclosed herein that include an improved outer sealing member for reducing perivalvular leakage, as well as related methods and apparatuses including such prosthetic valves. In several embodiments, the disclosed prosthetic valves are configured as replacement heart valves for implantation into a subject.

In one representative embodiment, an implantable prosthetic valve can comprise an annular frame, a leaflet structure positioned within the frame and secured thereto, an annular sealing member positioned around an outer surface of the frame, and an outer skirt positioned around an outer surface of the sealing member and secured to the frame. The annular frame can comprise an inflow end and an outflow end and can be radially collapsible and expandable between a radially collapsed configuration and a radially expanded configuration. The annular sealing member can have a periodic, undulating shape.

In some embodiments, the sealing member can be secured directly to the frame.

In some embodiments, the sealing member can be secured to an inner surface of the outer skirt.

In some embodiments, the sealing member can have a zig-zag shape.

In some embodiments, the sealing member can comprise a plurality of first angled portions having a first orientation with respect to the frame and a plurality of second angled portions having a second orientation with respect to the frame. Each first angled portion can be connected to a second angled portion at an apex such that there is an angle between each first angled portion and a connected second angled portion.

In some embodiments, at least one of the apices can have a relatively pointed edge.

In some embodiments, at least one of the apices can have a rounded edge.

In some embodiments, the angle can be less than 90 degrees.

In some embodiments, the angle can be greater than 90 degrees.

In some embodiments, the angled can be 90 degrees.

In some embodiments, the outer skirt can have a plurality of openings.

In some embodiments, the openings can be axially aligned with the apices.

In another representative embodiment, an implantable prosthetic valve can comprise an annular frame, a leaflet structure positioned within the frame and secured thereto, an outer skirt positioned around an outer surface of the frame and secured thereto, and an annular sealing member positioned around an outer surface of the outer skirt and secured thereto. The annular frame can comprise an inflow end and an outflow end and can be radially collapsible and expandable between a radially collapsed configuration and a radially expanded configuration.

In some embodiments, the sealing member can have a zig-zag shape.

In some embodiments, the sealing member can comprise a plurality of first angled portions having a first orientation with respect to the frame and a plurality of second angled portions having a second orientation with respect to the frame. Each first angled portion can be connected to a second angled portion at an apex such that there is an angle between each first angled portion and a connected second angled portion.

In some embodiments, at least one of the apices can have a relatively pointed edge.

In some embodiments, at least one of the apices can have a rounded edge.

In some embodiments, the angle can be less than 90 degrees.

In some embodiments, the angled can be greater than 90 degrees.

In some embodiments, the angled can be 90 degrees.

In some embodiments, the outer skirt can have a plurality of openings.

In some embodiments, the openings can be axially aligned with the apices.

In another representative embodiment, an implantable prosthetic valve can comprise an annular frame, a leaflet structure positioned within the frame and secured thereto, and an annular sealing member positioned around and conforming to an outer surface of the frame. The annular frame can comprise an inflow end and an outflow end and can be radially collapsible and expandable between a radially collapsed configuration and a radially expanded configuration. The annular sealing member can have a plurality of openings.

In some embodiments, the sealing member can comprise a plurality of circumferentially extending rows of openings.

In some embodiments, the sealing member can comprise a first row of openings and a second row of openings that is axially offset from the first row of openings.

In some embodiments, at least one of the openings can have a hexagonal shape.

In some embodiments, at least one of the openings can have a diamond shape.

In another representative embodiment, an implantable prosthetic valve can comprise an annular frame, a leaflet structure positioned within the frame and secured thereto, and an annular sealing member positioned around an outer surface of the frame. The annular frame can comprise an inflow end and an outflow end and can be radially collapsible and expandable between a radially collapsed configuration and a radially expanded configuration. The sealing member can comprise a plurality of first angled portions and a plurality of second angled portions such that the first and second angled portions form a plurality of v-shaped projections.

In some embodiments, the prosthetic valve can further comprise a plurality of straight first connecting portions extending between adjacent pairs of v-shaped projections at the bases of the first and second angled portions.

In some embodiments, the prosthetic valve can further comprise a plurality of straight second connecting portions extending between the first and second angled portions of each v-shaped projection.

In some embodiments, the second connecting portions can be axially offset from the first connecting portions.

In another representative embodiment, an implantable prosthetic valve can comprise an annular frame, a leaflet structure positioned within the frame and secured thereto, and an annular sealing member positioned around an outer surface of the frame. The annular frame can comprise an inflow end and an outflow end and can be radially collapsible and expandable between a radially collapsed configuration and a radially expanded configuration. The sealing member can have an undulating shape comprising three u-shaped sections, wherein each u-shaped section can circumscribe the frame through an angle of about 120 degrees.

In some embodiments, the leaflet structure can comprise three leaflets and the u-shaped sections can follow the shape of the inflow edges of the leaflets.

The foregoing and other objects, features, and advantages of the disclosure will become more apparent from the following detailed description, which proceeds with reference to the accompanying figures.

BRIEF DESCRIPTION OF THE DRAWINGS

FIGS. 4-10 show an exemplary frame of the prosthetic heart valve of FIG. 1.

FIGS. 11-12 show an exemplary inner skirt of the prosthetic heart valve of FIG. 1.

FIG. 13 shows the prosthetic heart valve of FIG. 1 in a collapsed configuration and mounted on an exemplary balloon catheter.

FIGS. 14-16 show the assembly of the inner skirt of FIG. 11 with the frame of FIG. 4.

DETAILED DESCRIPTION

Figures 1, 2, 3:
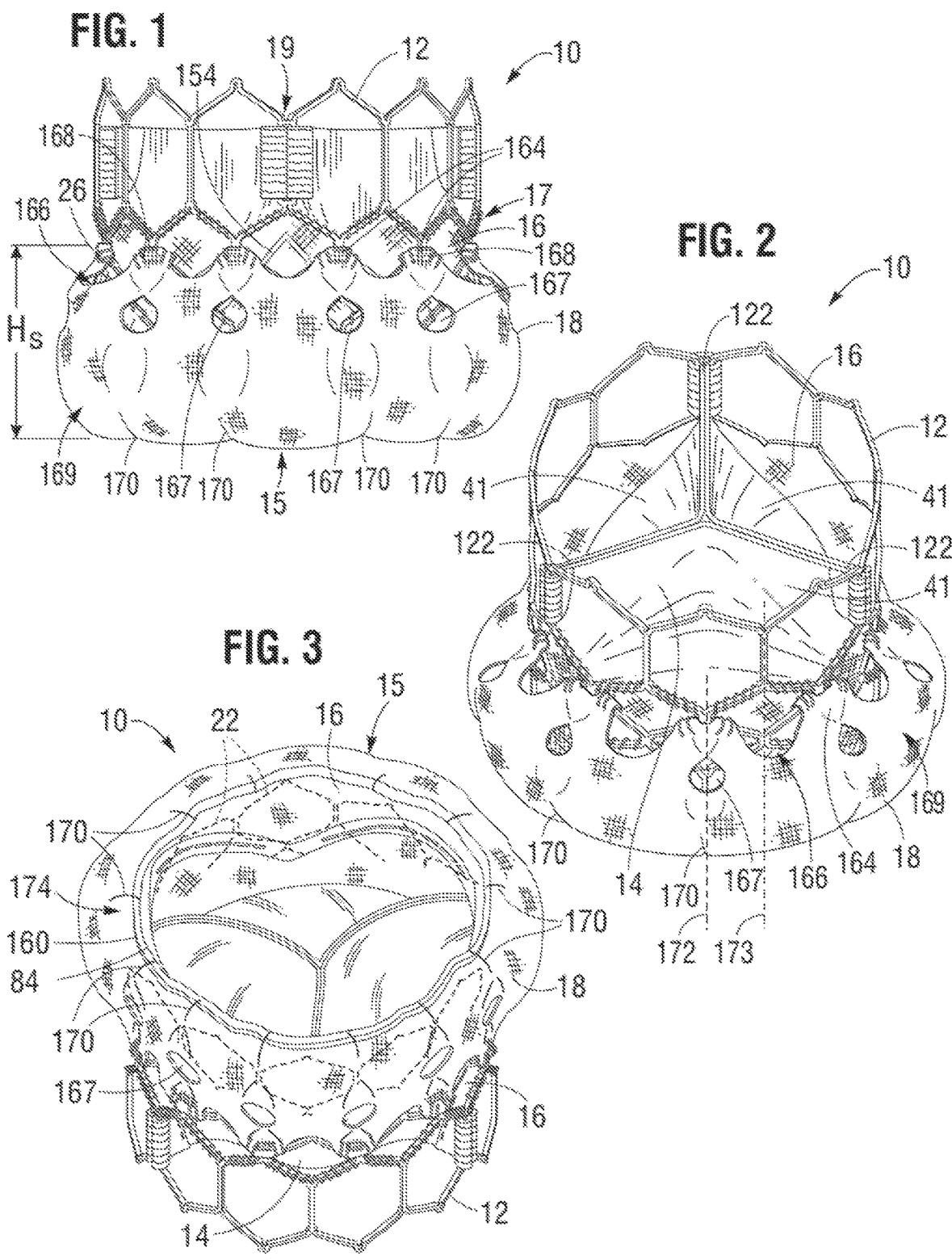
FIGS. 1-3 show an exemplary embodiment of a prosthetic heart valve.
Figures 9, 10:
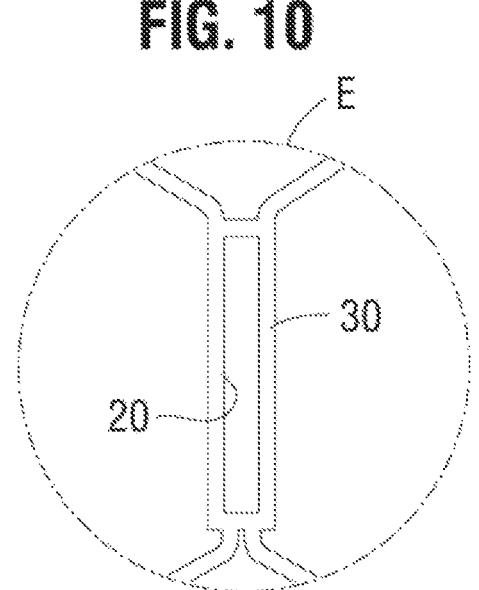

FIGS. 1-3 show various views of a prosthetic heart valve 10, according to one embodiment. The illustrated prosthetic valve is adapted to be implanted in the native aortic annulus, although in other embodiments it can be adapted to be implanted in the other native annuluses of the heart (e.g., the pulmonary, mitral, and tricuspid valves). The prosthetic valve can also be adapted to be implanted in other tubular organs or passageways in the body. The prosthetic valve 10 can have four main components: a stent or frame 12, a valvular structure 14, an inner skirt 16, and a perivalvular sealing means or sealing member. The prosthetic valve 10 can have an inflow end portion 15, an intermediate portion 17, and an outflow end portion 19. In the illustrated embodiment, the perivalvular sealing means comprises an outer skirt 18 (which can also be referred to as an outer sealing member).

The valvular structure 14 can comprise three leaflets 41, collectively forming a leaflet structure, which can be arranged to collapse in a tricuspid arrangement, as best shown in FIG. 2. The lower edge of leaflet structure 14 desirably has an undulating, curved scalloped shape (suture line 154 shown in FIG. 21 tracks the scalloped shape of the leaflet structure). By forming the leaflets with this scalloped geometry, stresses on the leaflets are reduced, which in turn improves durability of the prosthetic valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the prosthetic valve. The leaflets 41 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference in its entirety herein.

The bare frame 12 is shown in FIG. 4. The frame 12 can be formed with a plurality of circumferentially spaced slots, or commissure windows, 20 (three in the illustrated embodiment) that are adapted to connect to the commissures of the valvular structure 14 to the frame, as described in greater detail below. The frame 12 can be made of any of various suitable plastically-expandable materials (e.g., stainless steel, etc.) or self-expanding materials (e.g., nickel titanium alloy (NiTi), such as nitinol). When constructed of a plastically-expandable material, the frame 12 (and thus the prosthetic valve 10) can be crimped to a radially collapsed configuration on a delivery catheter and then expanded inside a patient by an inflatable balloon or equivalent expansion mechanism. When constructed of a self-expandable material, the frame 12 (and thus the prosthetic valve 10) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size.

Suitable plastically-expandable materials that can be used to form the frame 12 include, without limitation, stainless steel, a biocompatible, high-strength alloys (e.g., a cobalt-chromium or a nickel-cobalt-chromium alloys), polymers, or combinations thereof. In particular embodiments, frame 12 is made of a nickel-cobalt-chromium-molybdenum alloy, such as MP35N® alloy (SPS Technologies, Jenkintown, Pa.), which is equivalent to UNS R30035 alloy (covered by ASTM F562-02). MP35N® alloy/UNS R30035 alloy comprises 35% nickel, 35% cobalt, 20% chromium, and 10% molybdenum, by weight. When MP35N® alloy is used as the frame material, as compared to stainless steel, less material is needed to achieve the same or better performance in radial and crush force resistance, fatigue resistances, and corrosion resistance. Moreover, since less material is required, the crimped profile of the frame can be reduced, thereby providing a lower profile prosthetic valve assembly for percutaneous delivery to the treatment location in the body.

Referring to FIGS. 4 and 5, the frame 12 in the illustrated embodiment comprises a first, lower row I of angled struts 22 arranged end-to-end and extending circumferentially at the inflow end of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end of the frame. A plurality of substantially straight axially extending struts 34 can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28. FIGS. 6, 7, 8, 9, and 10 are enlarged views of the portions of the frame 12 identified by letters A, B, C, D, and E, respectively, in FIG. 5.

Each commissure window frame portion 30 connects to a respective commissure of the leaflet structure 14. As can be seen each frame portion 30 is secured at its upper and lower ends to the adjacent rows of struts to provide a robust configuration that enhances fatigue resistance under cyclic loading of the prosthetic valve compared to cantilevered struts for supporting the commissures of the leaflet structure. This configuration enables a reduction in the frame wall thickness to achieve a smaller crimped diameter of the prosthetic valve. In particular embodiments, the thickness T of the frame 12 (FIG. 4) measured between the inner diameter and outer diameter is about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 40. The openings 40 are relatively large and are sized to allow portions of the leaflet structure 14 to protrude, or bulge, into and/or through the openings 40 when the frame 12 is crimped in order to minimize the crimping profile.

As best shown in FIG. 7, the lower end of the strut 31 is connected to two struts 28 at a node or junction 44, and the upper end of the strut 31 is connected to two struts 32 at a node or junction 46. The strut 31 can have a thickness Si that is less than the thicknesses S2 of the junctions 44, 46. The junctions 44, 46, along with junctions 64, prevent full closure of openings 40. FIG. 13 shows the prosthetic valve 10 crimped on a balloon catheter. As can be seen, the geometry of the struts 31, and junctions 44, 46, and 64 assists in creating enough space in openings 40 in the collapsed configuration to allow portions of the prosthetic leaflets to protrude or bulge outwardly through openings. This allows the prosthetic valve to be crimped to a relatively smaller diameter than if all of the leaflet material were constrained within the crimped frame.

The frame 12 is configured to reduce, to prevent, or to minimize possible over-expansion of the prosthetic valve at a predetermined balloon pressure, especially at the outflow end portion of the frame, which supports the leaflet structure 14. In one aspect, the frame is configured to have relatively larger angles 42a, 42b, 42c, 42d, 42e between struts, as shown in FIG. 5. The larger the angle, the greater the force required to open (expand) the frame. As such, the angles between the struts of the frame can be selected to limit radial expansion of the frame at a given opening pressure (e.g., inflation pressure of the balloon). In particular embodiments, these angles are at least 110 degrees or greater when the frame is expanded to its functional size, and even more particularly these angles are up to about 120 degrees when the frame is expanded to its functional size.

In addition, the inflow and outflow ends of a frame generally tend to over-expand more so than the middle portion of the frame due to the "dog-boning" effect of the balloon used to expand the prosthetic valve. To protect against over-expansion of the leaflet structure 14, the leaflet structure desirably is secured to the frame 12 below the upper row of struts 32, as best shown in FIG. 1. Thus, in the event that the outflow end of the frame is over-expanded, the leaflet structure is positioned at a level below where over-expansion is likely to occur, thereby protecting the leaflet structure from over-expansion.

In one type of prosthetic valve construction, portions of the leaflets protrude longitudinally beyond the outflow end of the frame when the prosthetic valve is crimped if the leaflets are connected too close to the distal end of the frame. If the delivery catheter on which the crimped prosthetic valve is mounted includes a pushing mechanism or stop member that pushes against or abuts the outflow end of the prosthetic valve (for example, to maintain the position of the crimped prosthetic valve on the delivery catheter), the pushing member or stop member can damage the portions of the exposed leaflets that extend beyond the outflow end of the frame. Another benefit of connecting the leaflets at a location spaced away from the outflow end of the frame is that when the prosthetic valve is crimped on a delivery catheter, the outflow end of the frame 12 rather than the leaflets 41 is the proximal-most component of the prosthetic valve 10. As such, if the delivery catheter includes a pushing mechanism or stop member that pushes against or abuts the outflow end of the prosthetic valve, the pushing mechanism or stop member contacts the outflow end of the frame, and not leaflets 41, so as to avoid damage to the leaflets.

Also, as can be seen in FIG. 5, the openings 36 of the lowermost row of openings in the frame are relatively larger than the openings 38 of the two intermediate rows of openings. This allows the frame, when crimped, to assume an overall tapered shape that tapers from a maximum diameter at the outflow end of the prosthetic valve to a minimum diameter at the inflow end of the prosthetic valve. When crimped, the frame 12 can have a reduced diameter region extending along a portion of the frame adjacent the inflow end of the frame that generally corresponds to the region of the frame covered by the outer skirt 18. In some embodiments, the reduced diameter region is reduced compared to the diameter of the upper portion of the frame (which is not covered by the outer skirt) such that the outer skirt 18 does not increase the overall crimp profile of the prosthetic valve. When the prosthetic valve is deployed, the frame can expand to the generally cylindrical shape shown in FIG. 4. In one example, the frame of a 26-mm prosthetic valve, when crimped, had a first diameter of 14 French at the outflow end of the prosthetic valve and a second diameter of 12 French at the inflow end of the prosthetic valve.

The main functions of the inner skirt 16 are to assist in securing the valvular structure 14 to the frame 12 and to assist in forming a good seal between the prosthetic valve and the native annulus by blocking the flow of blood through the open cells of the frame 12 below the lower edge of the leaflets. The inner skirt 16 desirably comprises a tough, tear resistant material such as polyethylene terephthalate (PET), although various other synthetic materials or natural materials (e.g., pericardial tissue) can be used. The thickness of the skirt desirably is less than about 0.15 mm (about 6 mil), and desirably less than about 0.1 mm (about 4 mil), and even more desirably about 0.05 mm (about 2 mil). In particular embodiments, the skirt 16 can have a variable thickness, for example, the skirt can be thicker at least one of its edges than at its center. In one implementation, the skirt 16 can comprise a PET skirt having a thickness of about 0.07 mm at its edges and about 0.06 mm at its center. The thinner skirt can provide for better crimping performances while still providing good sealing.

Figure 20:
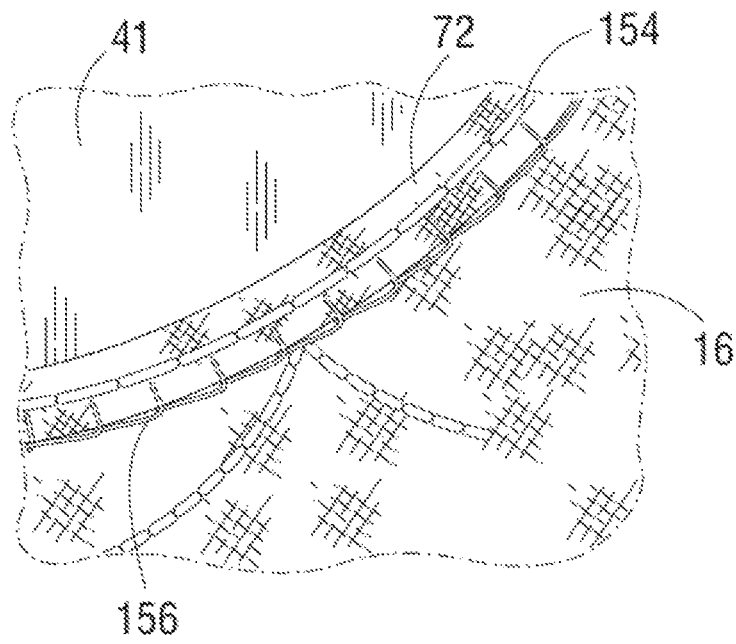
FIGS. 20-21 show the assembly of the leaflet structure with the inner skirt along a lower edge of the leaflets.
Figure 21:
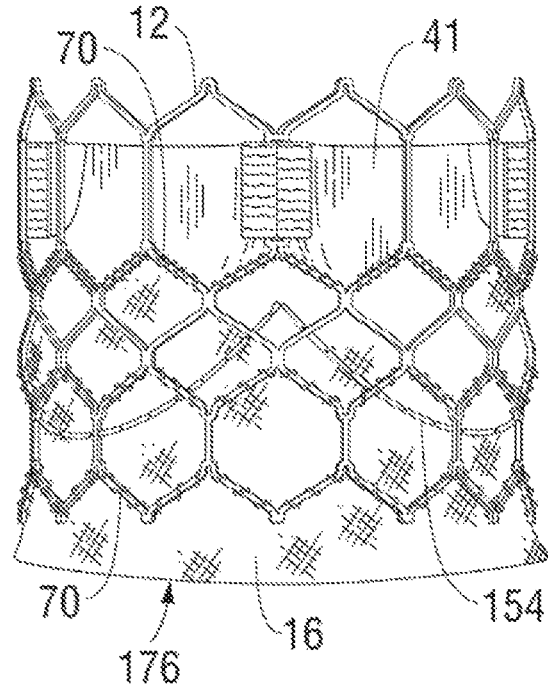

The skirt 16 can be secured to the inside of frame 12 via sutures 70, as shown in FIG. 21. Valvular structure 14 can be attached to the skirt via one or more reinforcing strips 72 (which collectively can form a sleeve), for example thin, PET reinforcing strips, discussed below, which enables a secure suturing and protects the pericardial tissue of the leaflet structure from tears. Valvular structure 14 can be sandwiched between skirt 16 and the thin PET strips 72 as shown in FIG. 20. Sutures 154, which secure the PET strip and the leaflet structure 14 to skirt 16, can be any suitable suture, such as Ethibond Excel® PET suture (Johnson & Johnson, New Brunswick, N.J.). Sutures 154 desirably track the curvature of the bottom edge of leaflet structure 14, as described in more detail below.

Some fabric skirts comprise a weave of warp and weft fibers that extend perpendicularly to each other and with one set of the fibers extending longitudinally between the upper and lower edges of the skirt. When the metal frame to which such a fabric skirt is secured is radially compressed, the overall axial length of the frame increases. However, a fabric skirt with limited elasticity cannot elongate along with the frame and therefore tends to deform the struts of the frame and to prevent uniform crimping.

Referring to FIG. 12, in one embodiment, the skirt 16 desirably is woven from a first set of fibers, or yarns or strands, 78 and a second set of fibers, or yarns or strands, 80, both of which are non-perpendicular to the upper edge 82 and the lower edge 84 of the skirt. In particular embodiments, the first set of fibers 78 and the second set of fibers 80 extend at angles of about 45 degrees (e.g., 15-75 degrees or 30-60 degrees) relative to the upper and lower edges 82, 84. For example, the skirt 16 can be formed by weaving the fibers at 45 degree angles relative to the upper and lower edges of the fabric. Alternatively, the skirt 16 can be diagonally cut (cut on a bias) from a vertically woven fabric (where the fibers extend perpendicularly to the edges of the material) such that the fibers extend at 45 degree angles relative to the cut upper and lower edges of the skirt. As further shown in FIG. 12, the opposing short edges 86, 88 of the skirt desirably are non-perpendicular to the upper and lower edges 82, 84. For example, the short edges 86, 88 desirably extend at angles of about 45 degrees relative to the upper and lower edges and therefore are aligned with the first set of fibers 78. Therefore the overall general shape of the skirt can be that of a rhomboid or parallelogram.

FIGS. 14 and 15 show the inner skirt 16 after opposing short edge portions 90, 92 have been sewn together to form the annular shape of the skirt. As shown, the edge portion 90 can be placed in an overlapping relationship relative to the opposite edge portion 92, and the two edge portions can be sewn together with a diagonally extending suture line 94 that is parallel to short edges 86, 88. The upper edge portion of the inner skirt 16 can be formed with a plurality of projections 96 that define an undulating shape that generally follows the shape or contour of the fourth row of struts 28 immediately adjacent the lower ends of axial struts 31. In this manner, as best shown in FIG. 16, the upper edge of the inner skirt 16 can be tightly secured to struts 28 with sutures 70. The inner skirt 16 can also be formed with slits 98 to facilitate attachment of the skirt to the frame. Slits 98 can be dimensioned so as to allow an upper edge portion of the inner skirt 16 to be partially wrapped around struts 28 and to reduce stresses in the skirt during the attachment procedure. For example, in the illustrated embodiment, the inner skirt 16 is placed on the inside of frame 12 and an upper edge portion of the skirt is wrapped around the upper surfaces of struts 28 and secured in place with sutures 70. Wrapping the upper edge portion of the inner skirt 16 around struts 28 in this manner provides for a stronger and more durable attachment of the skirt to the frame. The inner skirt 16 can also be secured to the first, second, and/or third rows of struts 22, 24, and 26, respectively, with sutures 70.

Referring again to FIG. 12, due to the angled orientation of the fibers relative to the upper and lower edges in this embodiment, the skirt can undergo greater elongation in the axial direction (i.e., in a direction from the upper edge 82 to the lower edge 84).

Thus, when the metal frame 12 is crimped (as shown in FIG. 13), the inner skirt 16 can elongate in the axial direction along with the frame and therefore provide a more uniform and predictable crimping profile. Each cell of the metal frame in the illustrated embodiment includes at least four angled struts that rotate towards the axial direction on crimping (e.g., the angled struts become more aligned with the length of the frame). The angled struts of each cell function as a mechanism for rotating the fibers of the skirt in the same direction of the struts, allowing the skirt to elongate along the length of the struts. This allows for greater elongation of the skirt and avoids undesirable deformation of the struts when the prosthetic valve is crimped.

In addition, the spacing between the woven fibers or yarns can be increased to facilitate elongation of the skirt in the axial direction. For example, for a PET inner skirt 16 formed from 20-denier yarn, the yarn density can be about 15% to about 30% lower than in a typical PET skirt. In some examples, the yarn spacing of the inner skirt 16 can be from about 60 yarns per cm (about 155 yarns per inch) to about 70 yarns per cm (about 180 yarns per inch), such as about 63 yarns per cm (about 160 yarns per inch), whereas in a typical PET skirt the yarn spacing can be from about 85 yarns per cm (about 217 yarns per inch) to about 97 yarns per cm (about 247 yarns per inch). The oblique edges 86, 88 promote a uniform and even distribution of the fabric material along inner circumference of the frame during crimping so as to facilitate uniform crimping to the smallest possible diameter. Additionally, cutting diagonal sutures in a vertical manner may leave loose fringes along the cut edges. The oblique edges 86, 88 help minimize this from occurring.

In alternative embodiments, the skirt can be formed from woven elastic fibers that can stretch in the axial direction during crimping of the prosthetic valve. The warp and weft fibers can run perpendicularly and parallel to the upper and lower edges of the skirt, or alternatively, they can extend at angles between 0 and 90 degrees relative to the upper and lower edges of the skirt, as described above.

The inner skirt 16 can be sutured to the frame 12 at locations away from the suture line 154 so that the skirt can be more pliable in that area. This configuration can avoid stress concentrations at the suture line 154, which attaches the lower edges of the leaflets to the inner skirt 16.

As noted above, the leaflet structure 14 in the illustrated embodiment includes three flexible leaflets 41 (although a greater or a smaller number of leaflets can be used). Additional information regarding the leaflets, as well as additional information regarding skirt material, can be found, for example, in U.S. patent application Ser. No. 14/704,861, filed May 5, 2015, which is incorporated by reference in its entirety.

The leaflets 41 can be secured to one another at their adjacent sides to form commissures 122 of the leaflet structure. A plurality of flexible connectors 124 (one of which is shown in FIG. 17) can be used to interconnect pairs of adjacent sides of the leaflets and to connect the leaflets to the commissure window frame portions 30 (FIG. 5).

Figures 17, 18, 19:
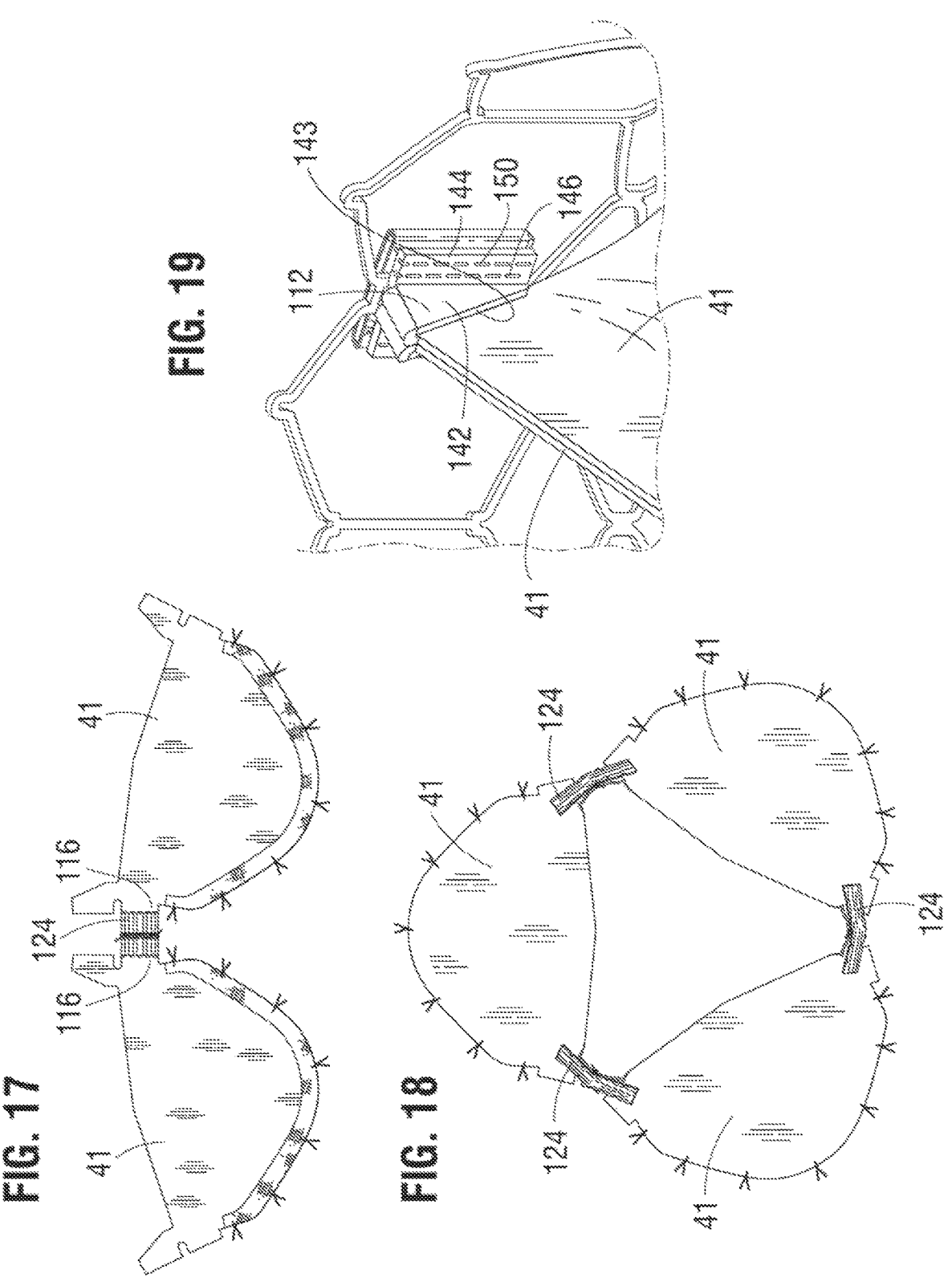
FIGS. 17-18 show the assembly of an exemplary leaflet structure.
FIG. 19 shows the assembly of commissure portions of the leaflet structure with window frame portions of the frame.

FIG. 17 shows the adjacent sides of two leaflets 41 interconnected by a flexible connector 124. Three leaflets 41 can be secured to each other side-to-side using three flexible connectors 124, as shown in FIG. 18. Additional information regarding connecting the leaflets to each other, as well as connecting the leaflets to the frame, can be found, for example, in U.S. Patent Application Publication No. 2012/0123529, which is incorporated by reference herein in its entirety.

As noted above, the inner skirt 16 can be used to assist in suturing the leaflet structure 14 to the frame. The inner skirt 16 can have an undulating temporary marking suture to guide the attachment of the lower edges of each leaflet 41. The inner skirt 16 itself can be sutured to the struts of the frame 12 using sutures 70, as noted above, before securing the leaflet structure 14 to the skirt 16. The struts that intersect the marking suture desirably are not attached to the inner skirt 16. This allows the inner skirt 16 to be more pliable in the areas not secured to the frame and minimizes stress concentrations along the suture line that secures the lower edges of the leaflets to the skirt. As noted above, when the skirt is secured to the frame, the fibers 78, 80 of the skirt (see FIG. 12) generally align with the angled struts of the frame to promote uniform crimping and expansion of the frame.

FIG. 19 shows one specific approach for securing the commissure portions 122 of the leaflet structure 14 to the commissure window frame portions 30 of the frame. In this approach, the flexible connector 124 (FIG. 18) securing two adjacent sides of two leaflets is folded widthwise and the upper tab portions 112 are folded downwardly against the flexible connector. Each upper tab portion 112 is creased lengthwise (vertically) to assume an L-shape having an inner portion 142 folded against the inner surface of the leaflet and an outer portion 144 folded against the connector 124. The outer portion 144 can then be sutured to the connector 124 along a suture line 146. Next, the commissure tab assembly is inserted through the commissure window 20 of a corresponding window frame portion 30, and the folds outside of the window frame portion 30 can be sutured to portions 144.

FIG. 19 also shows that the folded down upper tab portions 112 can form a double layer of leaflet material at the commissures. The inner portions 142 of the upper tab portions 112 are positioned flat against layers of the two leaflets 41 forming the commissures, such that each commissure comprises four layers of leaflet material just inside of the window frames 30. This four-layered portion of the commissures can be more resistant to bending, or articulating, than the portion of the leaflets 41 just radially inward from the relatively more-rigid four-layered portion. This causes the leaflets 41 to articulate primarily at inner edges 143 of the folded-down inner portions 142 in response to blood flowing through the prosthetic valve during operation within the body, as opposed to articulating about or proximal to the axial struts of the window frames 30. Because the leaflets articulate at a location spaced radially inwardly from the window frames 30, the leaflets can avoid contact with and damage from the frame. However, under high forces, the four layered portion of the commissures can splay apart about a longitudinal axis adjacent to the window frame 30, with each inner portion 142 folding out against the respective outer portion 144. For example, this can occur when the prosthetic valve 10 is compressed and mounted onto a delivery shaft, allowing for a smaller crimped diameter. The four-layered portion of the commissures can also splay apart about the longitudinal axis when the balloon catheter is inflated during expansion of the prosthetic valve, which can relieve some of the pressure on the commissures caused by the balloon, reducing potential damage to the commissures during expansion.

After all three commissure tab assemblies are secured to respective window frame portions 30, the lower edges of the leaflets 41 between the commissure tab assemblies can be sutured to the inner skirt 16. For example, as shown in FIG. 20, each leaflet 41 can be sutured to the inner skirt 16 along suture line 154 using, for example, Ethibond Excel® PET thread. The sutures can be in-and-out sutures extending through each leaflet 41, the inner skirt 16, and each reinforcing strip 72. Each leaflet 41 and respective reinforcing strip 72 can be sewn separately to the inner skirt 16. In this manner, the lower edges of the leaflets are secured to the frame 12 via the inner skirt 16. As shown in FIG. 20, the leaflets can be further secured to the skirt with blanket sutures 156 that extend through each reinforcing strip 72, leaflet 41 and the inner skirt 16 while looping around the edges of the reinforcing strips 72 and leaflets 41. The blanket sutures 156 can be formed from PTFE suture material. FIG. 21 shows a side view of the frame 12, leaflet structure 14 and the inner skirt 16 after securing the leaflet structure 14 and the inner skirt 16 to the frame 12 and the leaflet structure 14 to the inner skirt 16.

Figures 22, 23:
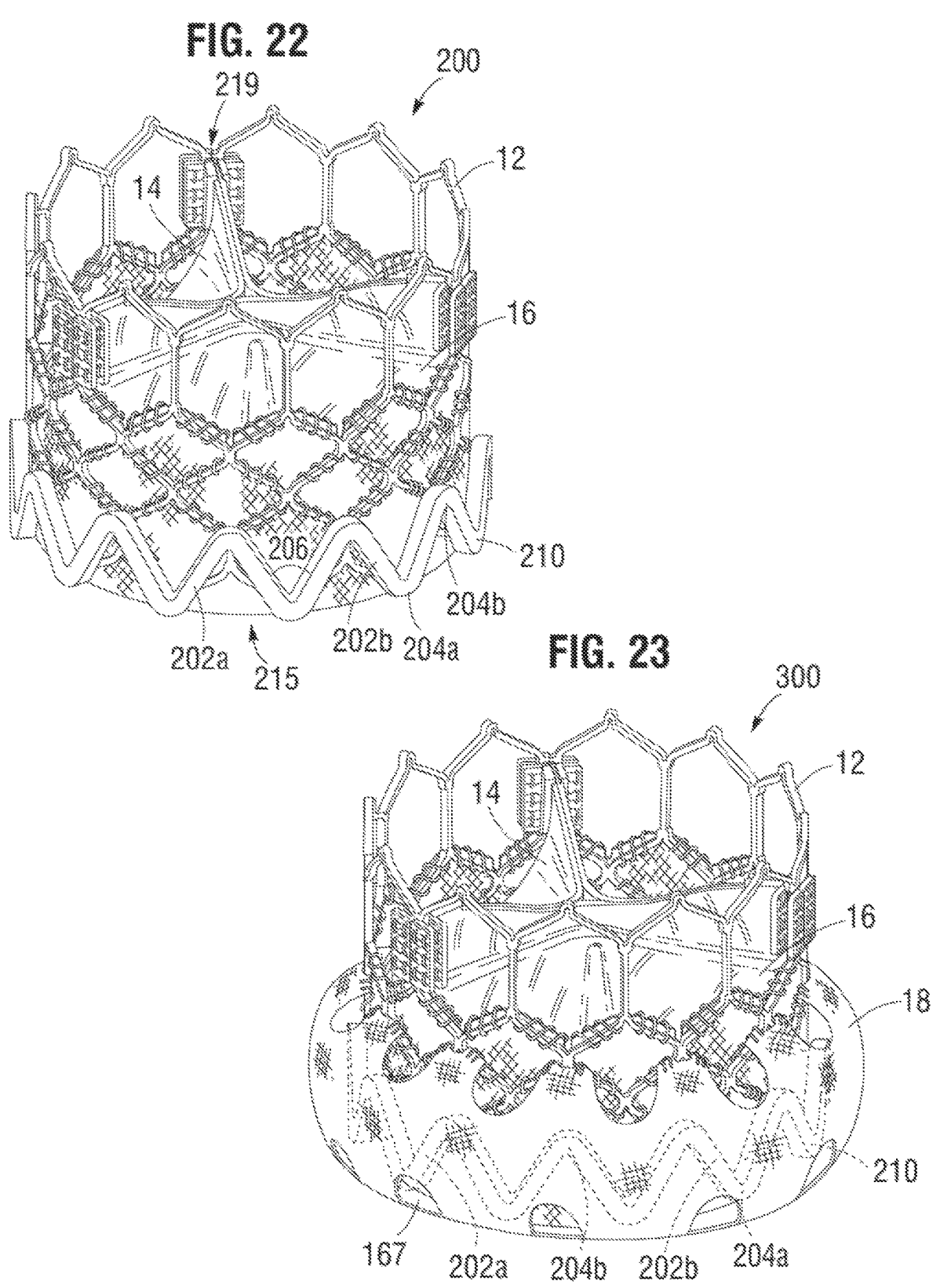
FIG. 22 shows an exemplary embodiment of a prosthetic heart valve in an expanded configuration.
FIG. 23 shows another exemplary embodiment of a prosthetic heart valve in an expanded configuration.

FIG. 22 shows another exemplary prosthetic heart valve 200 in an expanded configuration (e.g., when deployed in a patient). The prosthetic heart valve 200 of FIG. 22 can be the same as the prosthetic heart valve 10 of FIGS. 1-3 except that the outer skirt 18 of FIGS. 1-3 has been replaced by a sealing member 210 in FIG. 22. The prosthetic heart valve 200 can include a frame 12, a valvular structure 14, and an inner skirt 16, constructed in a manner similar to the prosthetic heart valve 10 of FIGS. 1-3. The prosthetic heart valve 200 can have an inflow end portion 215 and an outflow end portion 219 and can define an axial direction from the inflow end 215 to the outflow end 219. The sealing member 210 can be positioned annularly around an outer surface of the frame 12 and secured thereto.

The sealing member 210 desirably is sized and shaped to conform to the outer surface of the frame 12. In other words, the inner surface of the sealing member 210 can lie flat against the outer surface of the frame 12 and can form a snug fit with the outer surface of the frame.

In particular embodiments, the sealing member 210 is made from a material that can absorb blood, thus causing the sealing member 210 to expand as explained in further detail below. The sealing member 210 can be made from, for example, any of various fabrics that are woven, braided or knitted from various types of natural or synthetic fibers, including but not limited to PET fibers (e.g., Dacron), polyester fibers, or polyamide fibers, etc. In certain embodiments, the fabric can be a plush fabric (such as a velour, cloth or towel) having loops or piles of fibers or yarns. In other embodiments, the sealing member 210 can be made from any of various non-woven fabrics, such as felt. In still other embodiments, the sealing member 210 can be made from a sponge or foam material, such as polyurethane sponge. Other sealing members disclosed herein (including those shown in FIGS. 23-33) can be made from the same materials.

In the illustrated example of FIG. 22, the sealing member 210 has a zig-zag shape around the outer surface of the frame 12, wherein the sealing member 210 comprises a plurality of first angled portions 202a having a first orientation with respect to the frame 12, a plurality of second angled portions 202b having a second orientation with respect to the frame 12, a plurality of inflow apices 204a where the first angled portions 202a meet the second angled portions 202b at a location near the inflow end 215, and a plurality of outflow apices 204b where the first angled portions 202a meet the second angled portions 202b at a location relatively closer to the outflow end 219. The first orientation is such that the first angled portions 202a are angled in a direction offset from the axial direction of the prosthetic heart valve 200 in a clockwise direction by an angle of less than 90 degrees. The second orientation is such that the second angled portions 202b are angled in a direction offset from the axial direction of the prosthetic heart valve 200 in a counterclockwise direction by an angle of less than 90 degrees.

In the illustrated example of FIG. 22, the shape of the sealing member 210 is periodic around the surface of the frame 12. In some examples, the shape of the sealing member 210 can be sinusoidal or undulating around the surface of the frame 12. In some examples, the inflow apices 204a and the outflow apices 204b can comprise sharp points or angles such that there is an abrupt transition between the first angled portions 202a and the second angled portions 202b. In other examples, the inflow apices 204a and the outflow apices 204b can comprise rounded edges such that there is a gradual transition between the first angled portions 202a and the second angled portions 202b. In the illustrated example of FIG. 22, the sealing member 210 comprises one continuous piece of material. In other examples, the sealing member 210 can comprise multiple pieces of material attached together around the frame 12. The first angled portions 202a and the second angled portions 202b form an angle 206 between them. In the illustrated example of FIG. 22, the angle 206 is less than 90 degrees. In other examples, the angle 206 can be greater than or equal to 90 degrees.

In the illustrated example of FIG. 22, the inflow apices 204a are aligned with vertical lines 172 of the frame 12 and the outflow apices 204b are aligned with vertical lines 173. Alternatively, the inflow and outflow apices 204a, 204b can be aligned with any portion of the frame 12. In the illustrated example of FIG. 22, the sealing member 210 is secured to the frame 12 at the lowermost rows I and II of struts 22, 24. In other embodiments, the sealing member 210 can be secured to the frame 12 at struts 26, 28, and/or 32 over rows III, IV, and/or V. In the illustrated embodiment of FIG. 22, the sealing member 210 is secured to the frame 12 with sutures. Alternatively, the sealing member 210 can be secured to the frame 12 with adhesive and/or ultrasonic welding in addition to or in lieu of sutures.

The zig-zag shaped sealing member 210 gives the prosthetic heart valve 200 a relatively low crimped profile. That is, when the prosthetic heart valve 200 is crimped into a collapsed configuration, the angle 206 is reduced and the first and second angled portions 202a, 202b are positioned closer together than when the prosthetic heart valve 200 is in the expanded configuration without overlapping or bunching, which could potentially damage or impair the proper operation of the prosthetic heart valve 200.

The material of the sealing member 210 can absorb blood when the prosthetic heart valve 200 is implanted in a native valve of a patient and expanded to its expanded configuration. When the sealing member 210 absorbs blood, the material of the sealing member 210 expands. This expansion of the sealing member 210 can help seal any gaps between the prosthetic heart valve 200 and the native anatomy and help prevent perivalvular leakage.

FIG. 23 shows another exemplary prosthetic heart valve 300 in an expanded configuration (e.g., when deployed in a patient). Referring to FIG. 23, the prosthetic heart valve 300 is the same as the prosthetic heart valve 200 of FIG. 22 except that outer skirt 18 of FIGS. 1-3 is positioned and secured to an outer surface of the frame 12. The outer skirt 18 can be secured to the frame 12 in a similar manner as described with respect to the prosthetic heart valve 10 of FIGS. 1-3. The outer skirt 18 can be secured to the frame 12 and can be positioned around an outer surface of the sealing member 210. The outer skirt 18 can comprise openings 167 that can be aligned with the outflow apices 204b as shown in FIG. 23. Alternatively, the openings 167 can be aligned with the inflow apices 204a or the openings 167 can have any other orientation with respect to the inflow and outflow apices 204a, 204b.

When the prosthetic heart valve 300 is implanted in a native valve of a patient and expanded to its expanded configuration, antegrade blood can flow between the frame 12 and the outer skirt 18. Antegrade blood can also flow through the openings 167. This antegrade blood can be absorbed by the sealing member 210, which can expand and cause the outer skirt 18 to better seal any gaps between the prosthetic heart valve 300 and the native anatomy of the patient.

Figure 24:
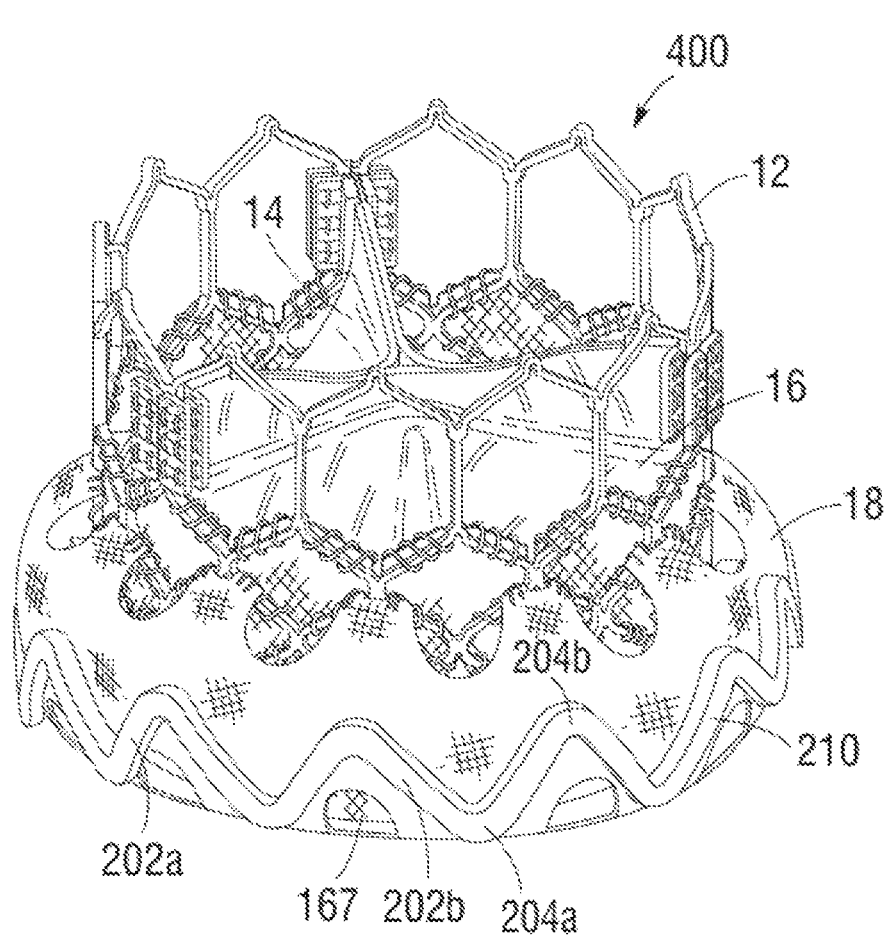
FIG. 24 shows another exemplary embodiment of a prosthetic heart valve in an expanded configuration.

FIG. 24 shows another prosthetic heart valve 400 in an expanded configuration (e.g., when deployed in a patient). Referring to FIG. 24, the prosthetic heart valve 400 is the same as the prosthetic heart valve 300 of FIG. 23 except that outer skirt 18 is positioned between the frame 12 and the sealing member 210 and the sealing member 210 is positioned around and secured to an outer surface of the sealing member 18. The sealing member 210 can be secured to the outer skirt 18 with sutures. Alternatively, the sealing member 210 can be secured to the outer skirt 18 with adhesive and/or ultrasonic welding in addition to or in lieu of sutures. In the illustrated embodiment of FIG. 24, the openings 167 are aligned with the outflow apices 204b. Alternatively, the openings 167 can be aligned with the inflow apices 204a or the openings 167 can have any other orientation with respect to the inflow and outflow apices 204a, 204b.

When the prosthetic heart valve 400 is implanted in a native valve of a patient and expanded to its expanded configuration, antegrade blood can flow between the frame 12 and the outer skirt 18 and through the openings 167. In addition, antegrade blood can be absorbed by the sealing member 210, which can expand and cause the outer skirt 18 to help seal any gaps between the prosthetic heart valve 400 and the native anatomy of the patient.

Figure 25:
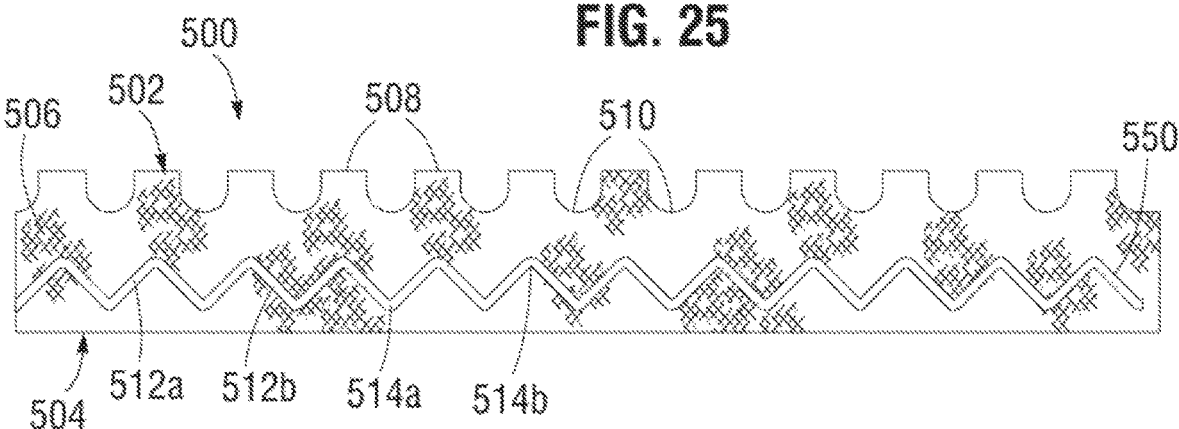
FIG. 25 shows an exemplary embodiment of an outer skirt.

FIG. 25 shows a flattened view of an outer skirt 500 prior to its attachment to a prosthetic heart valve. Referring to FIG. 25, the outer skirt 500 can comprise a first end portion 502 (i.e., the upper end portion as depicted in FIG. 25), a second end portion 504 (i.e., the lower end portion as depicted in FIG. 25), and an intermediate portion 506 disposed between the first and second end portions 502, 504. The first end portion 502 of the outer skirt 500 can include a plurality of alternating projections 508 and notches 510, or castellations. The intermediate portion 506 can include a sealing member 550 similar to sealing member 210 of FIGS. 22-24 secured thereto.

In the illustrated embodiment of FIG. 25, the sealing member 550 has a zig-zag shape along the length of the intermediate portion 506 of the outer skirt 500 similar to the zig-zag shape of sealing member 210 of FIGS. 22-24. The sealing member 550 can comprise first angled portions 512a, second angles portions 512b, inflow apices 514a, and outflow apices 514b. In the illustrated embodiment of FIG. 25, the inflow apices 514a are axially aligned with the notches 510 and the outflow apices 514b are axially aligned with the projections 508. In some embodiments, the inflow apices 514a can be axially aligned with the projections 508 and the outflow apices 514b can be axially aligned with the notches 510. In other embodiments, the inflow and outflow apices 514a, 514b can have any other orientation with respect to the projections 508 and notches 510. In the illustrated embodiment of FIG. 25, the sealing member 550 is secured to the outer skirt 500 skirt with sutures. Alternatively, the sealing member 550 can be secured to the outer skirt 500 with adhesive and/or ultrasonic welding in addition to or in lieu of sutures.

Figure 26:
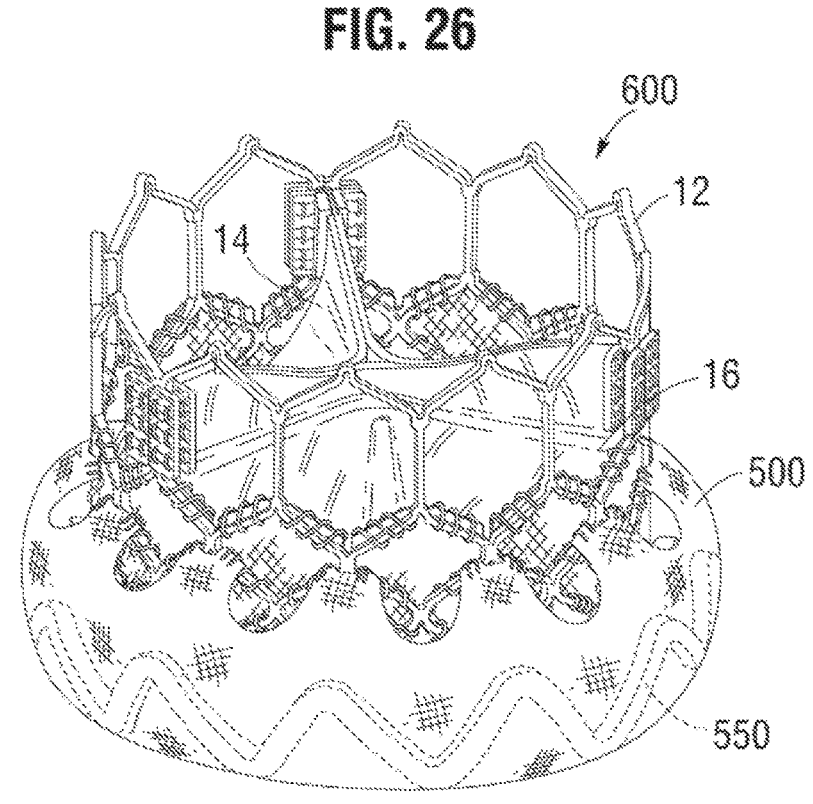
FIG. 26 shows an exemplary embodiment of a prosthetic heart valve that uses the outer skirt of FIG. 25.

FIG. 26 shows another exemplary prosthetic heart valve 600 in an expanded configuration (e.g., when deployed in a patient). Referring to FIG. 26, the prosthetic heart valve 600 is the same as prosthetic heart valve 10 of FIGS. 1-3 except that outer skirt 18 is replaced with the outer skirt 500 of FIG. 25. The outer skirt 18 can be secured to the frame 12 in a similar manner as described with respect to the prosthetic heart valve 10 of FIGS. 1-3. In the illustrated example of FIG. 26, the outer skirt 500 is positioned around an outer surface of the frame 12 and arranged such that the sealing member 550 is on the inside of the outer skirt 500 (i.e., the sealing member 550 is between the frame 12 and the skirt 500). In other embodiments, the outer skirt 500 can be arranged around the outer surface of the frame 12 such that the sealing member 550 is on the outside of the outer skirt 500. When the prosthetic heart valve 600 is implanted in a native valve of a patient and expanded to its expanded configuration, antegrade blood can flow between the frame 12 and the outer skirt 500. This antegrade blood can be absorbed by the sealing member 550, causing the sealing member 550 to expand and help the outer skirt 500 to seal any gaps between the prosthetic heart valve 600 and the native anatomy.

Figure 27:
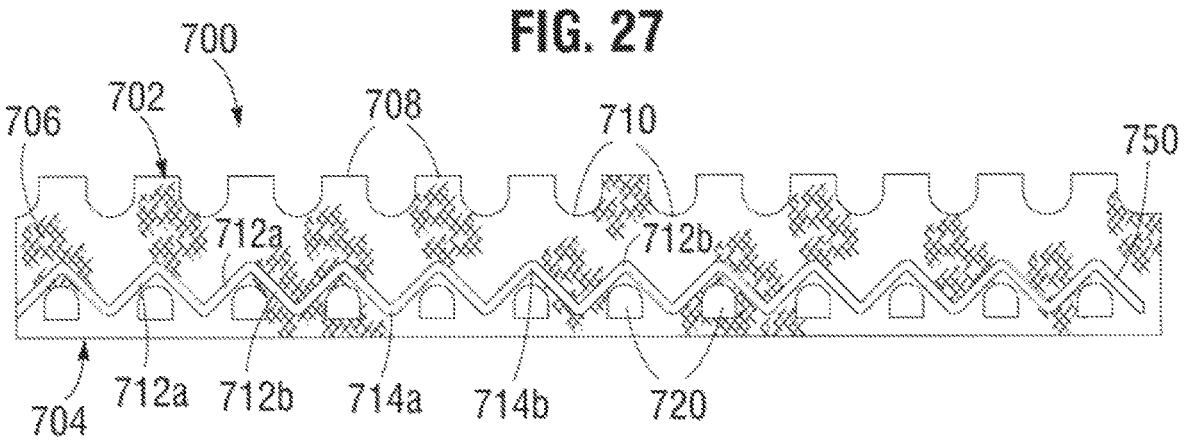
FIG. 27 shows another exemplary embodiment of an outer skirt.

FIG. 27 shows a flattened view of an outer skirt 700 prior to its attachment to a prosthetic heart valve. Referring to FIG. 27, the outer skirt 700 can comprise a first end portion 702 (i.e., the upper end portion as depicted in FIG. 27), a second end portion 704 (i.e., the lower end portion as depicted in FIG. 25), and an intermediate portion 706 disposed between the first and second end portions 702, 704. The first end portion 702 of the outer skirt 700 can include a plurality of alternating projections 708 and notches 710, or castellations. The intermediate portion 706 can include a sealing member 750 similar to sealing member 200 of FIGS. 22-24 secured thereto.

In the illustrated embodiment of FIG. 27, the sealing member 750 has a zig-zag shape along the length of the intermediate portion 706 of the outer skirt 700 similar to the zig-zag shape of sealing member 200 of FIGS. 22-24. The sealing member 750 can comprise first angled portions 712a, second angles portions 712b, inflow apices 714a, and outflow apices 714b. The sealing member 750 can further comprise a plurality of openings 720 in the intermediate portion 706. In the illustrated embodiment of FIG. 27, the openings 720 have a half oval shape. In other embodiments, the openings 720 can have a circular, teardrop, or any other shape. In the illustrated embodiment of FIG. 27, the openings 720 are axially aligned with the outflow apices 714*b* and the projections 708. In some embodiments, the openings 720 can be axially aligned with the inflow apices 714*a* and/or the notches 710. In other embodiments, the openings 720, the inflow and outflow apices 714*a,* 714*b,* the projections 708 and notches 710 can have any orientation with respect to each other. In the illustrated embodiment of FIG. 27, the sealing member 750 is secured to the outer skirt 700 skirt with sutures. Alternatively, the sealing member 750 can be secured to the outer skirt 700 with adhesive and/or ultrasonic welding in addition to or in lieu of sutures.

Figure 28:
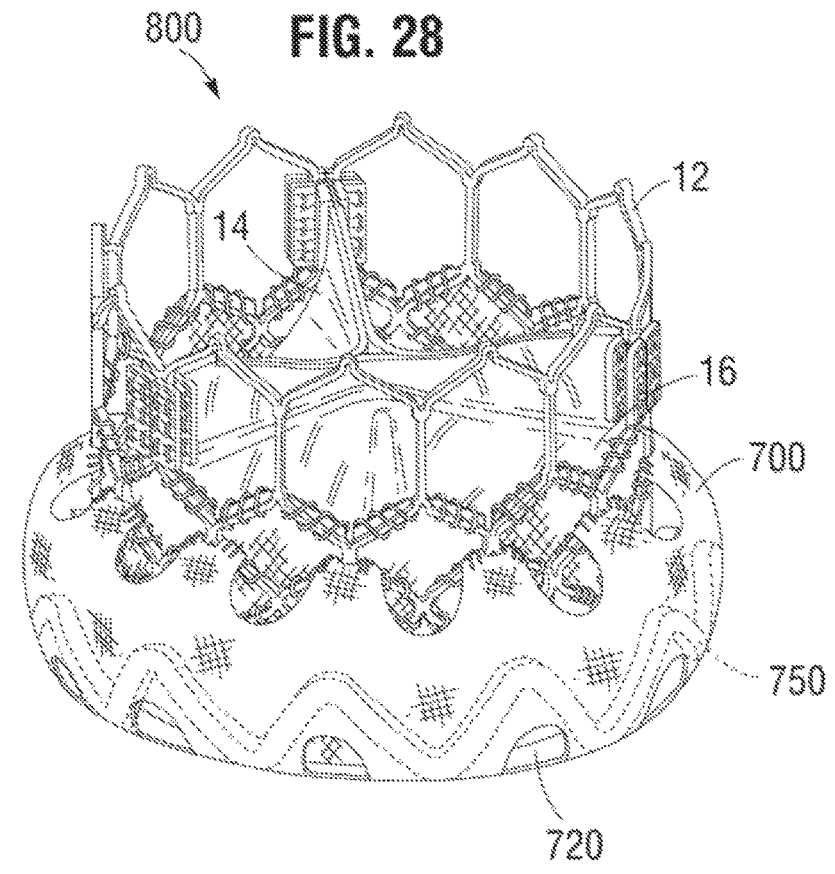
FIG. 28 shows an exemplary embodiment of a prosthetic heart valve that uses the outer skirt of FIG. 27.

FIG. 28 shows another exemplary prosthetic heart valve 800 in an expanded configuration (e.g., when deployed in a patient). Referring to FIG. 28, the prosthetic heart valve 800 is the same as prosthetic heart valve 600 of FIG. 26 except that outer skirt 500 is replaced with the outer skirt 700 of FIG. 27. The outer skirt 700 can be secured to the frame 12 in a similar manner as described with respect to the prosthetic heart valve 600 of FIG. 26. In the illustrated example of FIG. 28, the outer skirt 700 is positioned around an outer surface of the frame 12 and arranged such that the sealing member 750 is on the inside of the outer skirt 700 (i.e., the sealing member 750 is in contact with the frame 12). In other embodiments, the outer skirt 700 can be positioned around the outer surface of the frame 12 such that the sealing member 750 is on the outside of the outer skirt 700. When the prosthetic heart valve 800 is implanted in a native valve of a patient and expanded to its expanded configuration, antegrade blood can flow between the frame 12 and the outer skirt 700 and through the openings 720. This antegrade blood can be absorbed by the sealing member 750, causing the sealing member 750 to expand and help the outer skirt 700 to seal any gaps between the prosthetic heart valve 800 and the native anatomy.

Figure 29:
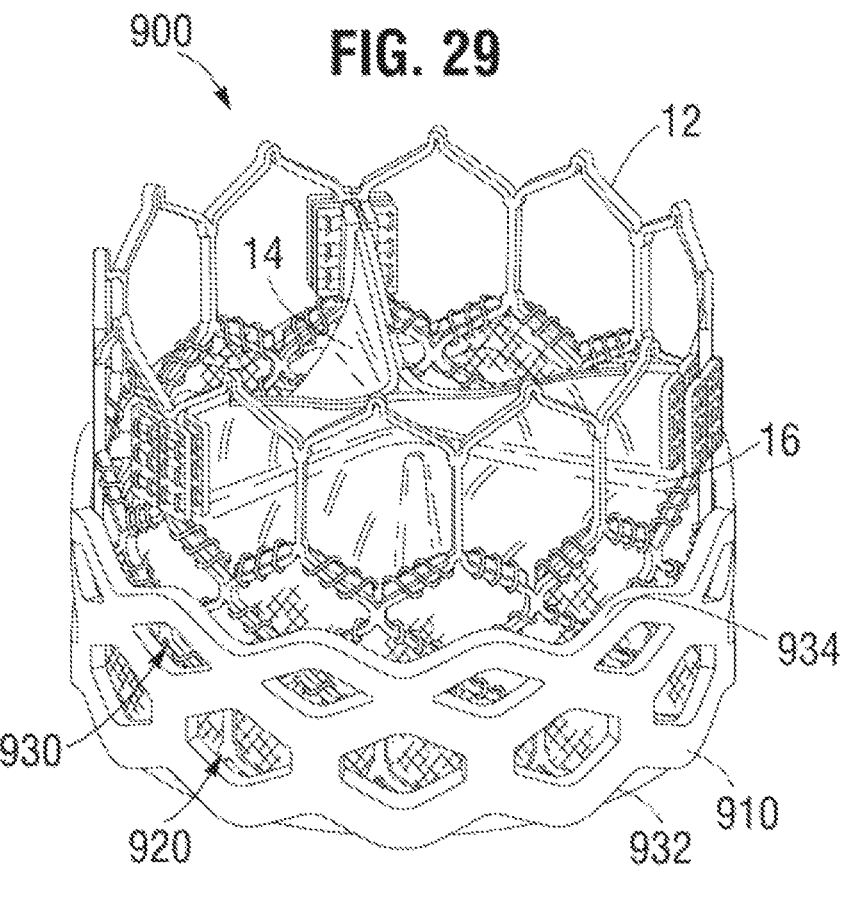
FIGS. 29-32 show exemplary prosthetic heart valves using other exemplary outer sealing members.

FIGS. 29-32 show other exemplary prosthetic heart valves. The prosthetic heart valves of FIGS. 29-32 can be the same as prosthetic heart valve 200 of FIG. 22 except with different sealing members replacing sealing member 210 of FIG. 22. FIG. 29 shows an exemplary prosthetic heart valve 900 having a sealing member 910 positioned annularly around frame 12 and being secured thereto in a similar manner that sealing member 210 is secured to the frame 12 in FIG. 22. The sealing member 910 has an axial span extending about from row I of struts to about row III of struts along the height of the frame 12, although the sealing member can be sized or shaped in other embodiments to extend over other portions of the frame.

The sealing member 910 desirably is sized and shaped to conform to the outer surface of the frame 12. In other words, the inner surface of the sealing member 910 can lie flat against the outer surface of the frame 12 and can form a snug fit with the outer surface of the frame.

The sealing member 910 can comprise one or more circumferentially extending rows of openings, such as a first row of a plurality of first openings 920 positioned annularly around the frame 12 and a second row of a plurality of second openings 930 positioned annularly around the frame 12. The sealing member 910 can be positioned such that the first openings 920 are positioned generally between rows I and II of the frame struts and the openings 930 are positioned generally between rows II and III of the frame struts, although the sealing member can be positioned at other locations on the frame in other embodiments. In the illustrated embodiment of FIG. 29, the first and second openings

920, 930 are axially offset from one another. Alternatively, the first and second openings 920, 930 can be axially aligned with each other.

In the illustrated embodiment, the first openings 920 are larger than the second openings 930. In other embodiments, the first openings 920 can be smaller than the second openings 930, or the same size as the second openings 930. In the illustrated embodiment, the first openings 920 are generally hexagonal in shape and the second openings 930 are diamond shaped. In other embodiments, the first and second openings can have any of various shapes, including, square, oval, circular, triangular, rectangular, or combinations thereof.

The sealing member 910 in the illustrated configuration has undulating inflow and outflow edges 932, 934, respectively. In alternative embodiments, one or more both of the inflow and outflow edges 932, 934 can be straight or can have various other configurations.

Figure 30:
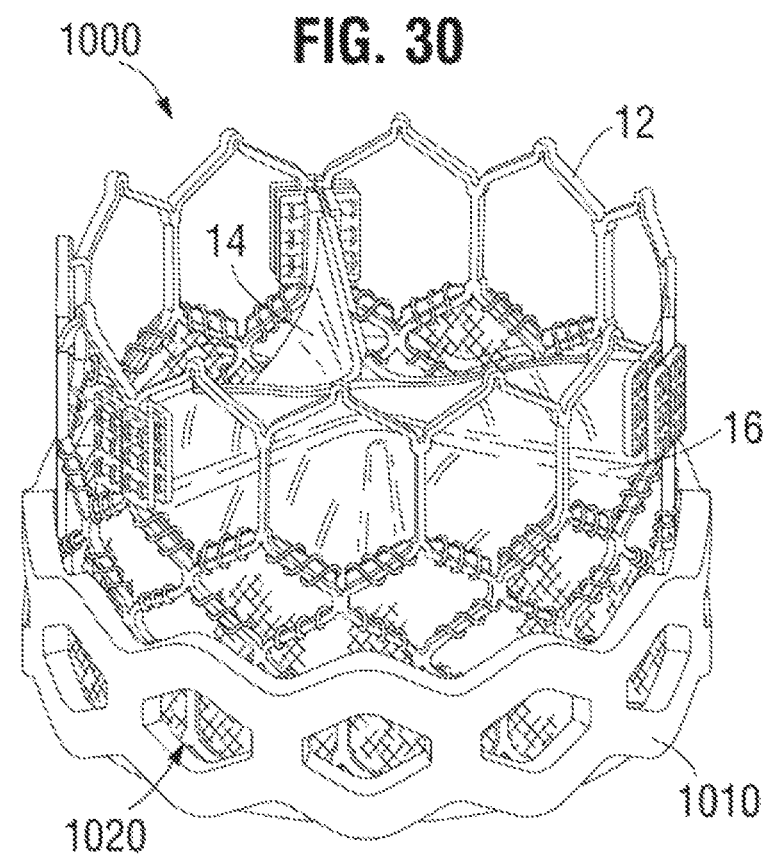

FIG. 30 shows an exemplary prosthetic heart valve 1000 having a sealing member 1010 positioned annularly around frame 12 and being secured thereto in a similar manner that sealing member 210 is secured to the frame 12 in FIG. 22. The sealing member 1010 has an axial span extending from about from row I of struts to about row II of struts along the frame 12. The sealing member 1010 has a plurality of circumferentially spaced openings 1020 positioned annularly around the frame 12. The sealing member 1010 can be positioned on the frame such that the openings are positioned generally between rows I and II of the frame struts as shown, although the sealing member can be positioned at other locations on the frame in other embodiments.

The sealing member 1010 desirably is sized and shaped to conform to the outer surface of the frame 12. In other words, the inner surface of the sealing member 1010 can lie flat against the outer surface of the frame 12 and can form a snug fit with the outer surface of the frame.

Figure 31:
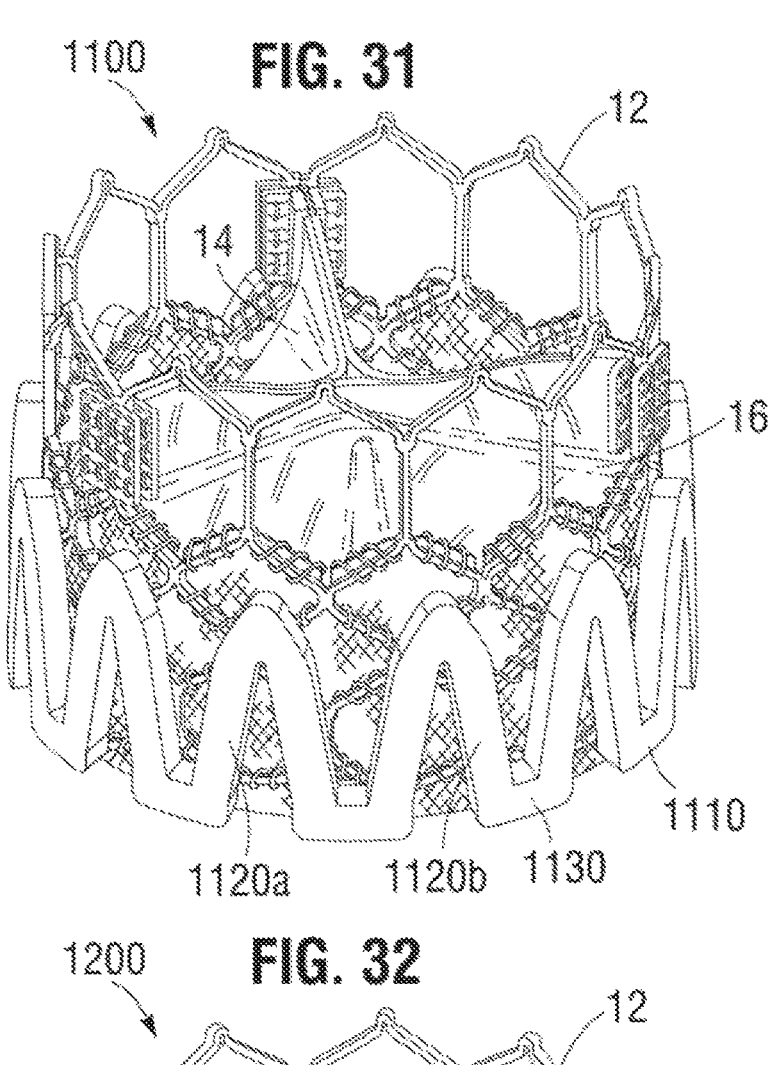

FIG. 31 shows an exemplary prosthetic heart valve 1100 having a sealing member 1110 positioned annularly around frame 12 and being secured thereto in a similar manner that sealing member 210 is secured to the frame 12 in FIG. 22. The sealing member 1110 in the illustrated embodiment comprises first angled or diagonally extending portions 1120*a* and second angled or diagonally extending portions 1120*b* forming a plurality of V or U-shaped projections. The sealing member 1110 can further include a plurality of straight connecting portions 1130 extending between and connecting adjacent pairs of V-shaped projections at the bases of first and second angled portions 1120*a,* 1120*b.*

The sealing member 1110 desirably is sized and shaped to conform to the outer surface of the frame 12. In other words, the inner surface of the sealing member 1110 can lie flat against the outer surface of the frame 12 and can form a snug fit with the outer surface of the frame.

Figure 32:
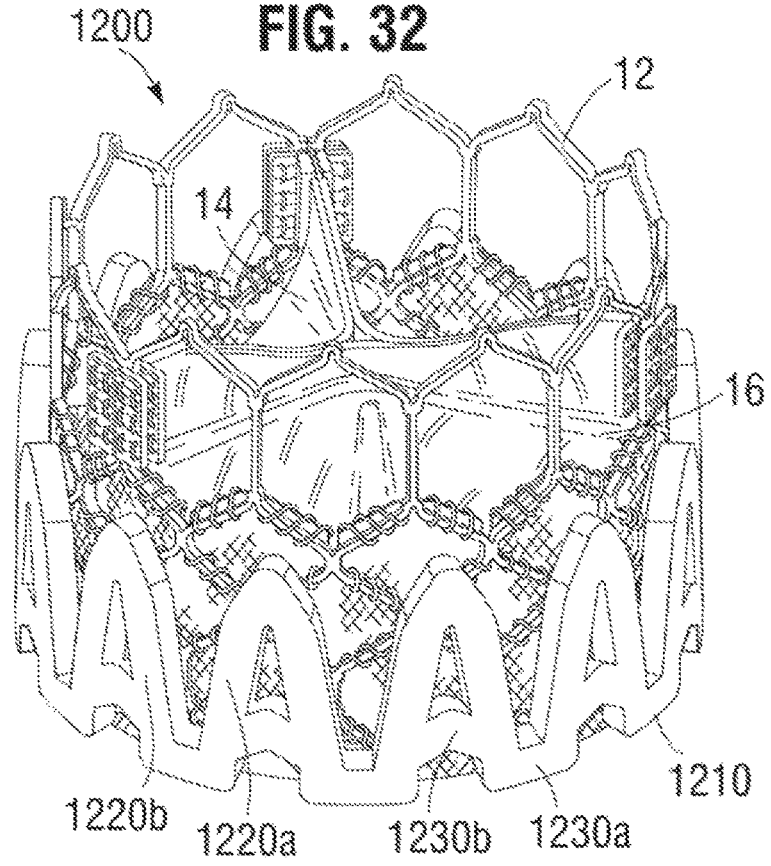

FIG. 32 shows an exemplary prosthetic heart valve 1200 having a sealing member 1210 positioned annularly around frame 12 and being secured thereto in a similar manner that sealing member 210 is secured to the frame 12 in FIG. 22. The sealing member 1210 comprises first angled or diagonally extending portions 1220*a* and second angled or diagonally extending portions 1220*b* forming a plurality of V or U-shaped projections. The sealing member 1210 can further include a plurality of first connecting portions 1230*a* extending between and connecting adjacent pairs of V-shaped projections at the bases of angled portions 1220*a,* 1220*b,* and a plurality of second connecting portions 1230*b* extending between and connecting the angled portions 1220*a,* 1220*b* of each V-shaped projection. The second connecting portions 1230b can be axially offset from the first connecting portions 1230a as shown (e.g., the second connecting portions can be located farther from the inlet end of the frame than the first connecting portions). Alternatively, the connecting portions can be located the same distance from the ends of the frame. In other embodiments, the sealing member 1210 can have various other shapes.

The sealing member 1210 desirably is sized and shaped to conform to the outer surface of the frame 12. In other words, the inner surface of the sealing member 1210 can lie flat against the outer surface of the frame 12 and can form a snug fit with the outer surface of the frame.

Figure 33:
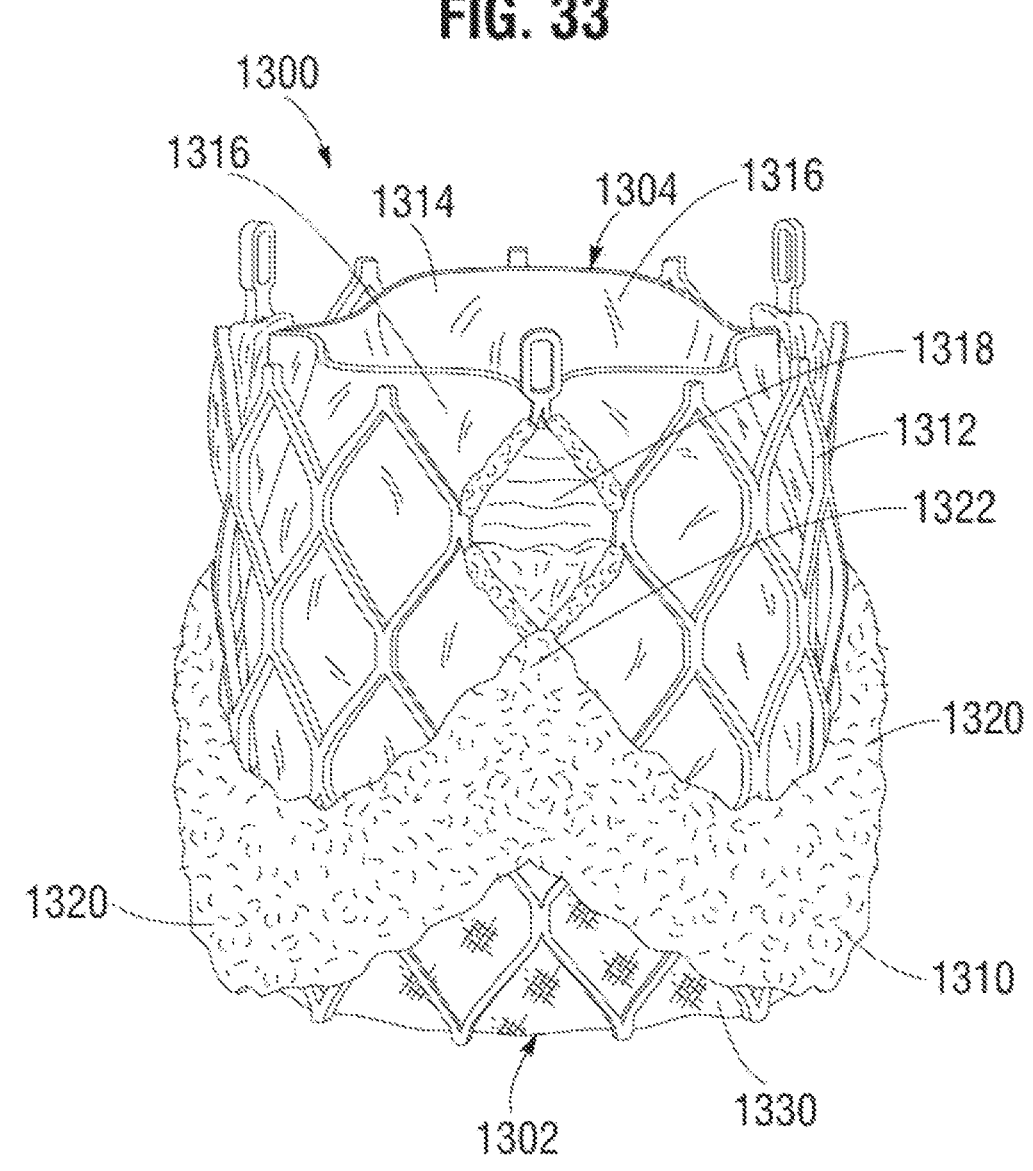
FIG. 33 shows another exemplary embodiment of a prosthetic heart valve in an expanded configuration.

FIG. 33 shows another exemplary prosthetic heart valve 1300 in an expanded configuration (e.g., when deployed in a patient). Referring to FIG. 33, the prosthetic heart valve 1300 comprises a frame 1312 and a valvular structure 1314. The valvular structure 1314 can include a plurality of leaflets 1316 that are connected to each other to form a plurality of commissures 1318 secured to the struts of the frame. The prosthetic heart valve 1300 can have an inflow end portion 1302 and an outflow end portion 1304. The prosthetic heart valve 1300 can also include an inner skirt 1330 secured to the inner surface of the frame. The frame 1312 can expand from a radially collapsed configuration to a radially expanded configuration in a manner similar to the frame 12 of FIGS. 1-3.

The sealing member 1310 desirably is sized and shaped to conform to the outer surface of the frame 12. In other words, the inner surface of the sealing member 1310 can lie flat against the outer surface of the frame 12 and can form a snug fit with the outer surface of the frame.

Additionally, the prosthetic heart valve 1300 in the illustrated embodiment of FIG. 33 further comprises a sealing member 1310 positioned annularly around an outer surface of the frame 12 and secured thereto. The sealing member 1310 can be made of a cloth material, a woven fabric, knitted fabric, plush fabric material (e.g., velour), or a towel material, or various other types of material as previously described. In the illustrated embodiment of FIG. 33, the sealing member 1310 has a scalloped or undulating shape around the outer surface of the frame 1312. The undulating shape of the sealing member 1310 helps minimize the overall crimp profile when the prosthetic heart valve is in a radially compressed state for delivery into a patient.

The sealing member 1310 in the illustrated embodiment comprises three U-shaped sections 1320 (two of which are visible in FIG. 33), with each section 1320 extending around or circumscribing the frame through an angle of about 120 degrees. The adjacent ends of adjacent sections 1320 meet at junctions 1322 that can be circumferentially aligned with corresponding commissures 1318. The U-shaped sections 1320 can be positioned on the frame so as to track or follow the shape of the inflow edges of the leaflets 1316 (which can have a scalloped shaped as shown in FIGS. 17-18). As shown, the inner skirt 1330 can be shaped to cover the openings in the frame 1312 only at locations below (upstream of) the commissures 1318 and between adjacent leaflets 1316. In this manner, the inner skirt 1330 need not cover openings in the frame 1312 above (downstream of) the inlet or cusp edges of the leaflets 1316, thereby minimizing the amount of material used to form the inner skirt, which can reduce the overall crimp profile. The inner skirt 1330 can have an undulating outflow edge that generally corresponds to the shape of the sealing member 1310 and the inlet edges of the leaflets 1316.

In alternative embodiments, the sealing member 1310 can be formed from more than three U-shaped sections 1320, each of which can circumscribe the frame through an angle less than 120 degrees In particular embodiments, the sealing member 1310 can absorb blood when the prosthetic heart valve 1300 is implanted in a native valve of a patient and expanded to its expanded configuration. This can help seal any gaps between the prosthetic heart valve 1310 and the native anatomy. In the illustrated embodiment of FIG. 33, the sealing member 1310 is secured to the frame 1312 with sutures. Alternatively, the sealing member 1310 can be secured to the frame 1312 with adhesive and/or ultrasonic welding in addition to or in lieu of sutures.

It should be noted that, in some embodiments, the outer skirts 500, 700 can comprise creases similar to the creases 170 of the outer skirt 18. The creases can be configured to facilitate uniform crimping and/or expansion and/or to reduce the crimped radial profile of a prosthetic heart valve in compressed delivery configuration. In some embodiments, the creases can be formed by ultrasonic welding.

Any of the prosthetic valves 10, 200, 300, 400, 600, 800, 900, 1000, 1100, 1200, or 1300 can be configured for and mounted on a suitable delivery apparatus for implantation in a patient. Several catheter-based delivery apparatuses can be used; a non-limiting example of a suitable catheter-based delivery apparatus includes that disclosed in U.S. Patent Application Publication No. 2013/0030519, which is incorporated by reference herein in its entirety, and U.S. Patent Application Publication No. 2012/0123529.

To implant a plastically-expandable prosthetic valve 200 or any of the other prosthetic valves disclosed herein within a patient, the prosthetic valve can be crimped on an elongated shaft 180 of a delivery apparatus, as best shown in FIG. 13. The prosthetic valve, together with the delivery apparatus, can form a delivery assembly for implanting the prosthetic valve 200 in a patient's body. The shaft 180 comprises an inflatable balloon 182 for expanding the prosthetic valve within the body. With the balloon 182 deflated, the prosthetic valve 200 can then be percutaneously delivered to a desired implantation location (e.g., a native aortic valve region). Once the prosthetic valve 200 is delivered to the implantation site (e.g., the native aortic valve) inside the body, the prosthetic valve 200 can be radially expanded to its functional state by inflating the balloon 182.

Alternatively, a self-expanding prosthetic valve 200 can be crimped to a radially collapsed configuration and restrained in the collapsed configuration by inserting the prosthetic valve 200 into a sheath or equivalent mechanism of a delivery catheter. The prosthetic valve 200 can then be percutaneously delivered to a desired implantation location. Once inside the body, the prosthetic valve 200 can be advanced from the delivery sheath, which allows the prosthetic valve to expand to its functional state.

Figure 34:
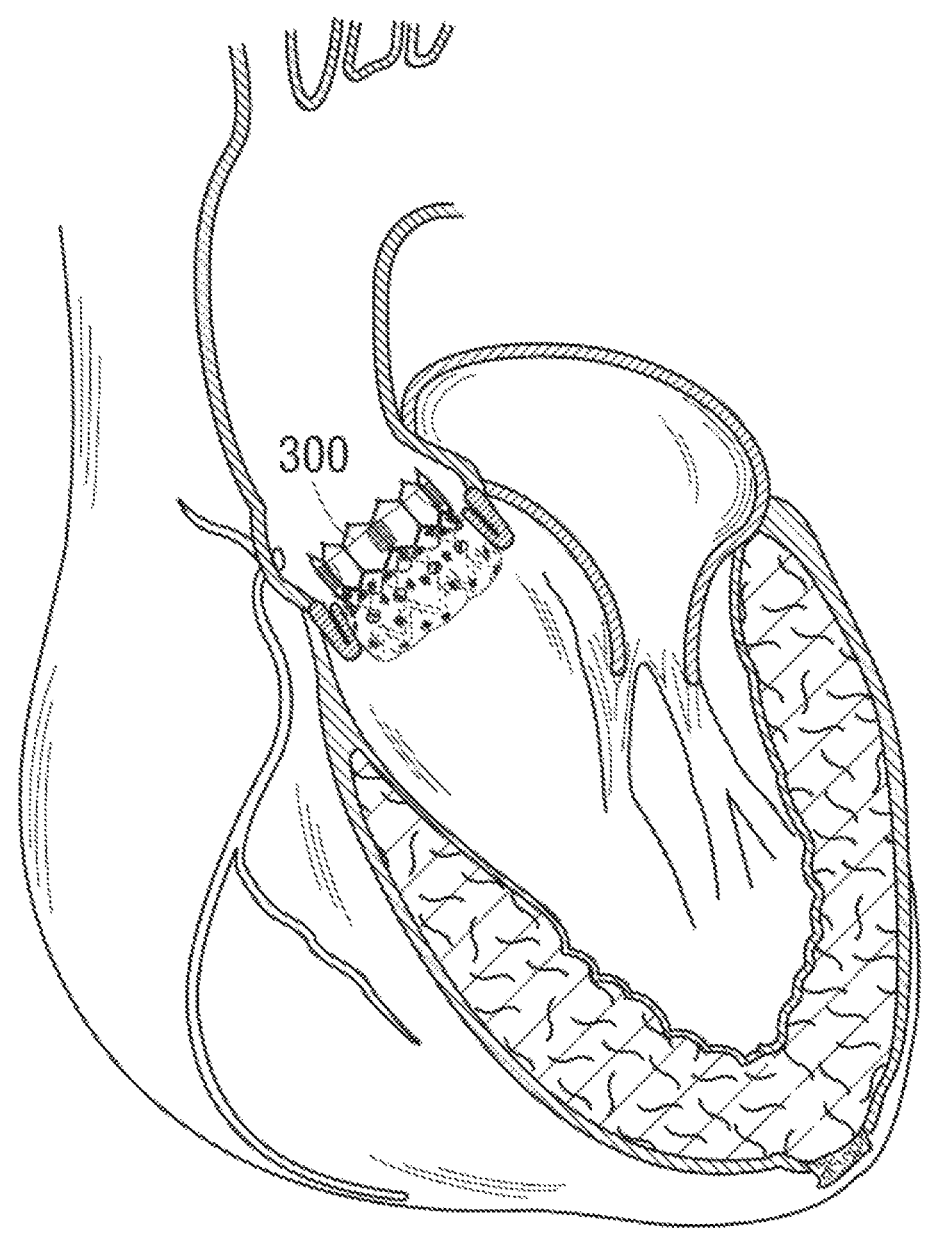
FIG. 34 shows an exemplary prosthetic heart valve implanted in the native aortic valve of a patient.

FIGS. 34-36 and 39 show various implantation positions for a prosthetic heart valve 300, including implantation within a dock or anchor placed inside the patient's body prior to valve implantation. Alternatively, the prosthetic heart valve 300 of FIGS. 34-36 and 39 can be replaced with prosthetic heart valve 200, 400, 600, 800, 900, 1000, 1100, 1200, or 1300. FIG. 34 shows the prosthetic heart valve 300 implanted in the native aortic valve of a patient.

Figure 35:
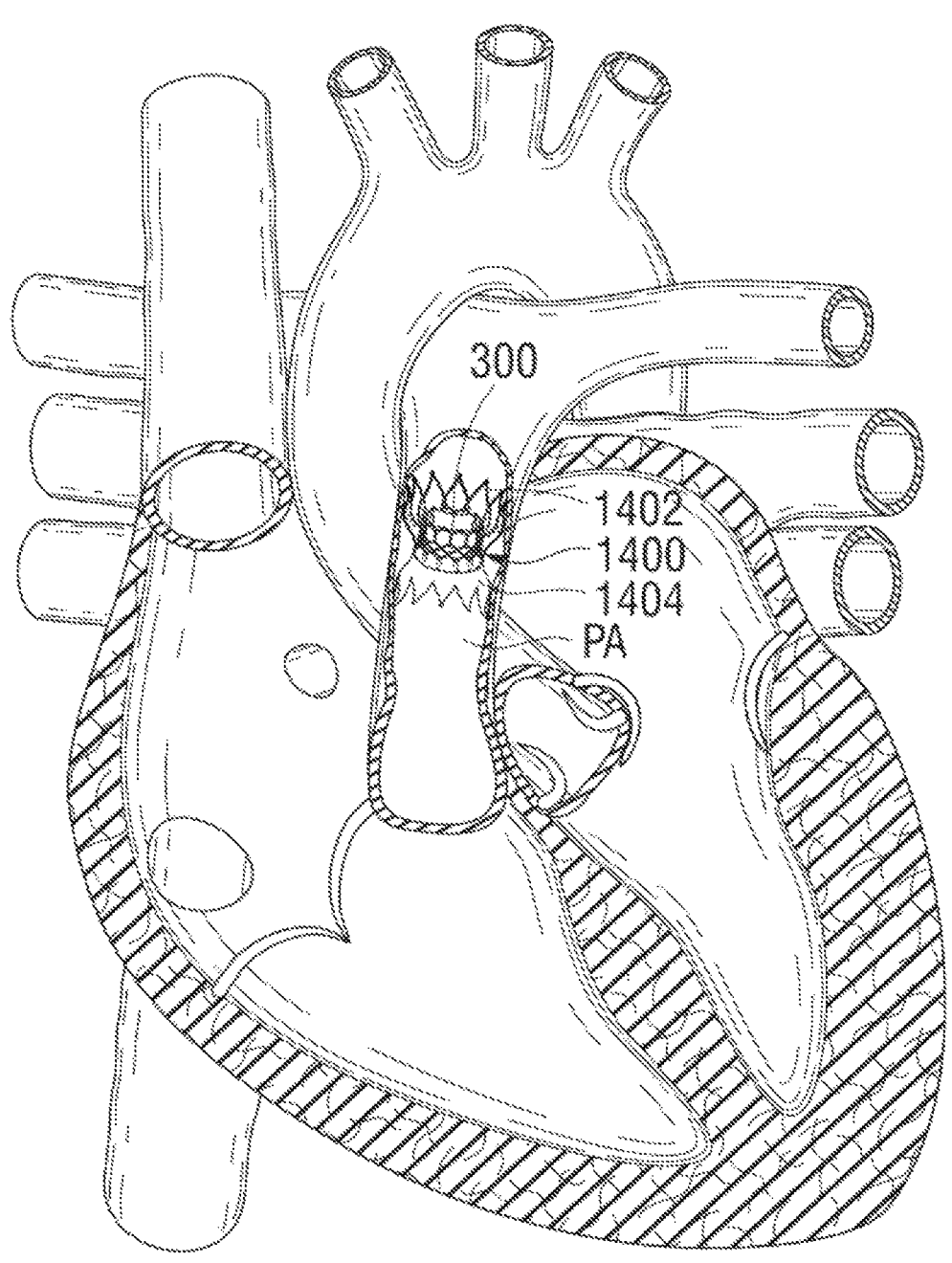
FIG. 35 shows an exemplary prosthetic heart valve and docking device implanted in the pulmonary artery of a patient.

FIG. 35 shows the prosthetic heart valve 300 implanted in the pulmonary artery of a patient for replacing or enhancing the function of a diseased pulmonary valve. Due to the variations in the size and shape of the native pulmonary valve and the pulmonary artery, the prosthetic valve 300 can be implanted within a radially expandable outer docking device 1400. The docking device 1400 can comprise a radially expandable and compressible annular stent 1402 and a sealing member 1404 that covers all or a portion of the stent and can extend across the inner surface and/or outer surface of the stent. The docking device 1400 is configured to engage the inner wall of the pulmonary artery and can accommodate variations in patient anatomy. The docking device 1400 also can compensate for the expanded prosthetic heart valve 300 being much smaller than vessel in which it is placed. The docking device 1400 also can be used to support a prosthetic valve in other areas of the patient's anatomy, such as, the inferior vena cava, superior vena cava, or the aorta. Further details of the docking device 1400 and methods for implanting the docking device and a prosthetic valve are disclosed, for example, in co-pending U.S. application Ser. No. 15/422,354, filed Feb. 1, 2017, which is incorporated herein by reference in its entirety.

Figure 36:
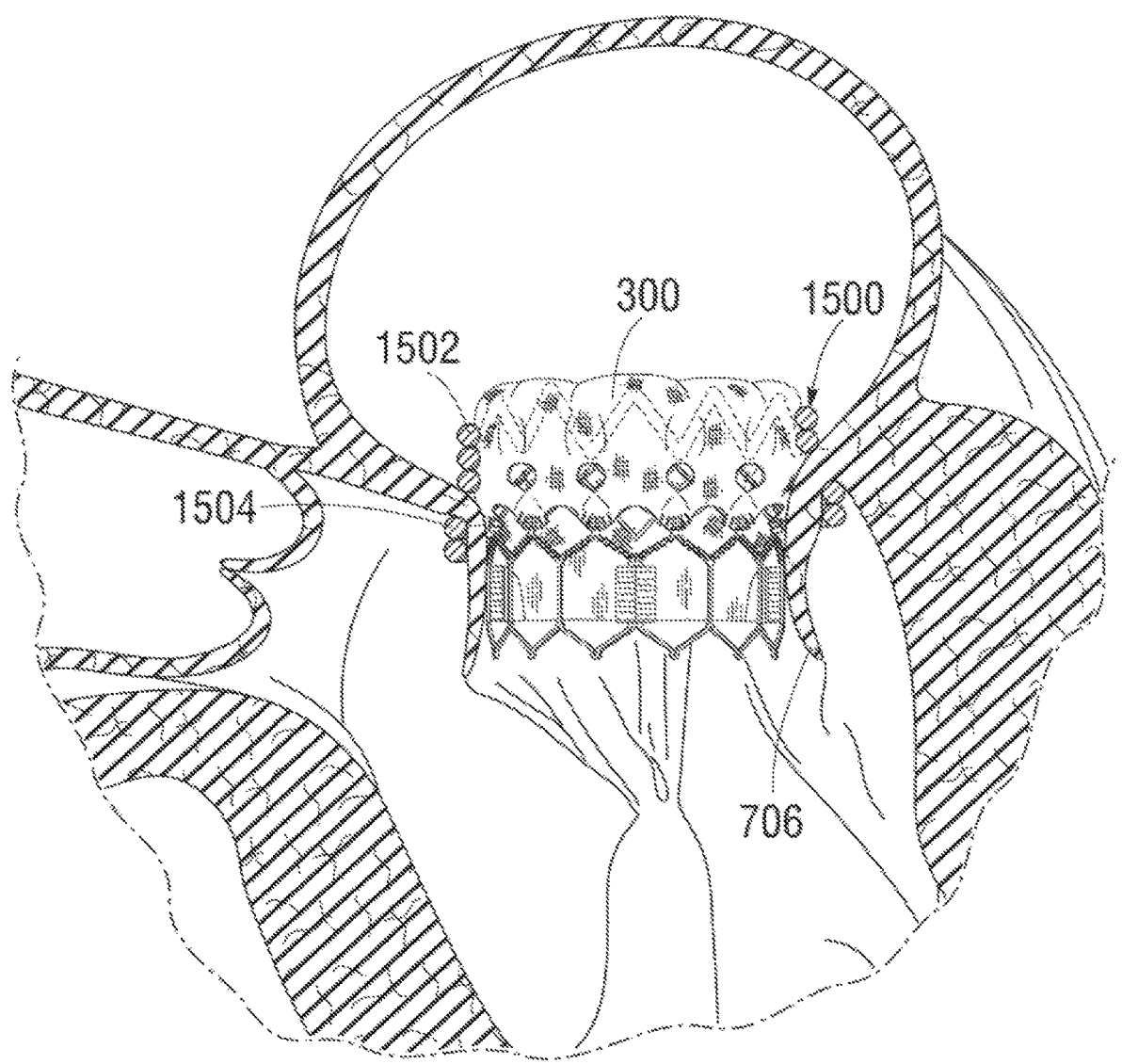
FIG. 36 shows an exemplary prosthetic heart valve and docking device implanted in the native mitral valve of a patient.

FIG. 36 shows the prosthetic heart valve 300 implanted in the native mitral valve of a patient using a docking device in the form of a helical anchor 1500. The helical anchor 1500 can include one or more coils 1502 deployed in left atrium and one or more coils 1504 deployed in the left ventricle and radially outside of the native mitral valve leaflets 1506. When the prosthetic valve 300 is deployed within the native valve, the native leaflets are compressed or pinched between the prosthetic valve 300 and the anchor 1500 to retain the prosthetic valve in place. Further details of the helical anchor 1500 and methods for implanting the anchor and a prosthetic valve are disclosed, for example, in co-pending U.S. Application No. 62/395,940, filed Sep. 16, 2016, which is incorporated herein by reference in its entirety.

Figures 37, 38:
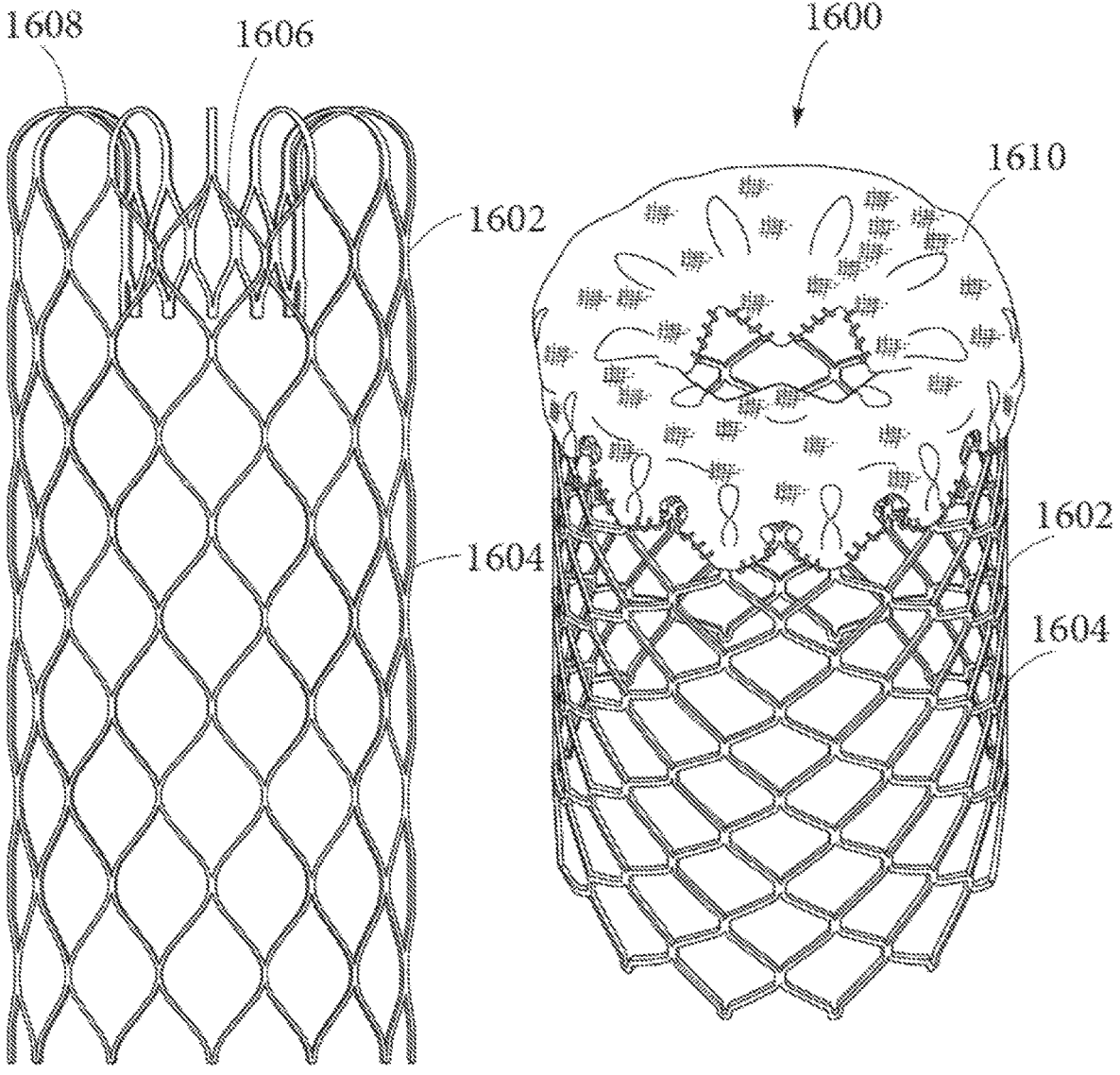
FIGS. 37-38 show an alternative embodiment of a docking device for a prosthetic valve.

FIGS. 37 and 38 show a docking device 1600 for a prosthetic heart valve, according to another embodiment. The docking device 1600 can include a radially expandable and compressible frame 1602 having an outer portion 1604, an inner portion 1606 disposed coaxially within one end portion of the outer portion 1604, and a curved transition portion 1608 extending between and connecting the inner portion 1606 and the outer portion 1604. The docking device 1600 can further include a sealing member 1610 extending over the inner surface of the inner portion 1606, a portion of the outer surface of the outer portion 1604 adjacent the inner portion 1606, and the transition portion 1608.

Figure 39:
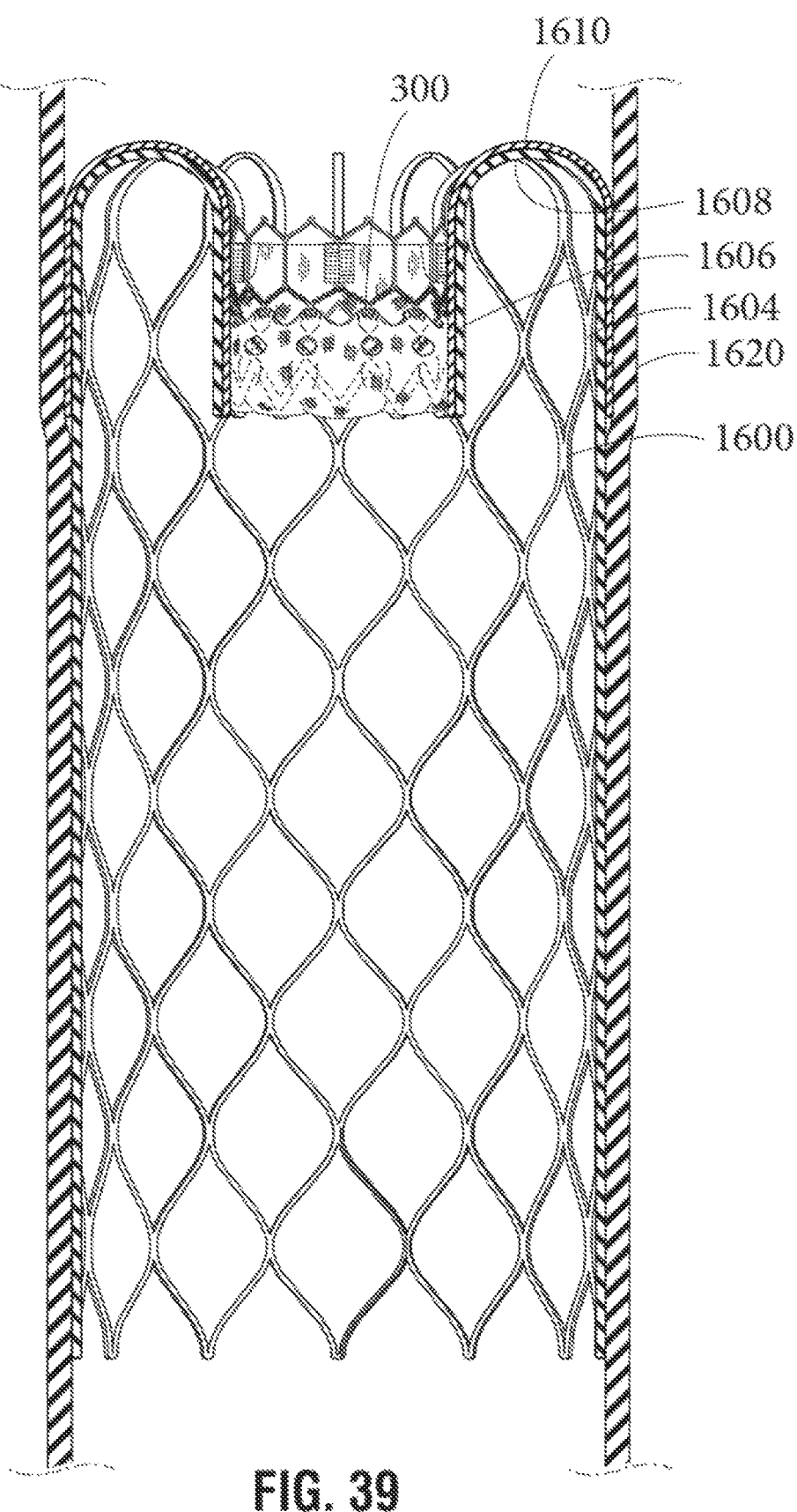
FIG. 39 shows an exemplary prosthetic heart valve and the docking device of FIGS. 37-38 implanted in the inferior vena cava of a patient.

FIG. 39 shows the docking device 1600 implanted in a vessel 1620, which can be, for example, the inferior vena cava, superior vena cava, or the ascending aorta. As shown, a prosthetic valve 300 can be deployed within the inner portion 1606 of the docking device 1600. Similar to the docking device 1400, the docking device 1600 can compensate for the expanded prosthetic heart valve 300 being much smaller than vessel in which it is placed. The docking device 1600 is particularly suited for implanting a prosthetic valve in the inferior vena cava for replacing or enhancing the function of the native tricuspid valve. Further details of the docking device 1600 and methods for implanting the docking device and a prosthetic valve are disclosed, for example, in co-pending U.S. application Ser. No. 16/034,794, filed Jul. 13, 2018, which is incorporated herein by reference.

General Considerations

It should be understood that the disclosed prosthetic valves can be implanted in any of the native annuluses of the heart (e.g., the pulmonary, mitral, and tricuspid annuluses), and can be used with any of various approaches (e.g., retrograde, antegrade, transseptal, transventricular, transatrial, etc.). The disclosed prostheses can also be implanted in other lumens of the body.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. For example, an outer sealing member for a prosthetic heart valve can include one or more features disclosed with respect to skirt 18, sealing member 210, sealing member skirt 500, skirt 700, sealing member 900, sealing member 1000, sealing member 1100, sealing member 1200, and/or sealing member 1300.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

As used in this application and in the claims, the singular forms "a," "an," and "the" include the plural forms unless the context clearly dictates otherwise. Additionally, the term "includes" means "comprises."

As used herein, the term "and/or" used between the last two of a list of elements means any one or more of the listed elements. For example, the phrase "A, B, and/or C" means "A", "B", "C", "A and B", "A and C", "B and C", or "A, B, and C".

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "coupled" and "associated" generally mean physically coupled or linked and does not exclude the presence of intermediate elements between the coupled or associated items absent specific contrary language.

As used herein, operations that occur "simultaneously" or "concurrently" occur generally at the same time as one another, although delays in the occurrence of one operation relative to the other due to, for example, spacing, play or backlash between components in a mechanical linkage such as threads, gears, etc., are expressly within the scope of the above terms, absent specific contrary language.

In view of the many possible embodiments to which the principles disclosed herein may be applied, it should be recognized that the illustrated embodiments are only preferred examples and should not be taken as limiting the scope of the disclosure. Rather, the scope of the disclosure is at least as broad as the following claims.

The invention claimed is:

1. An implantable prosthetic valve comprising:

an annular frame comprising an inflow end and an outflow end and being radially collapsible and expandable between a radially collapsed configuration and a radially expanded configuration;

a leaflet structure positioned within the frame and secured thereto;

an outer skirt positioned around an outer surface of the frame and secured thereto; and an annular sealing member disposed around and secured to an outer surface of the outer skirt, wherein the annular sealing member is formed of a plurality of interconnected, angled projections that extend radially outward from the outer surface of the outer skirt, the plurality of interconnected, angled projections comprising a plurality of first angled portions having a first orientation with respect to the frame and a plurality of second angled portions having a second orientation with respect to the frame, wherein the sealing member is further formed of a plurality of apices, wherein each first angled portion is connected to a second angled portion at an apex of the plurality of apices such that there is an angle between each first angled portion and a connected second angled portion, wherein the angled projections are made of a material that is configured to absorb blood and expand, and wherein the angled projections form an outermost radially facing surface of the sealing member for sealing against native tissue, and wherein the outer skirt has a plurality of openings that are axially aligned with a portion of apices of the plurality of apices at an end of the sealing member that is spaced away from the inflow end of the frame.

2. The prosthetic valve of claim 1, wherein the plurality of interconnected, angled projections forms a zig-zag shape.

3. The prosthetic valve of claim 1, wherein at least one of the plurality of apices has a relatively pointed edge.

4. The prosthetic valve of claim 1, wherein the angle is less than 90 degrees.

5. The prosthetic valve of claim 1, wherein the angle is greater than 90 degrees.

6. The prosthetic valve of claim 1, wherein the angle is 90 degrees.

7. The prosthetic valve of claim 1, wherein the sealing member undulates between an inflow end portion and an outflow end portion of the sealing member, around a circumference of the sealing member, wherein the inflow end portion is disposed at the inflow end of the frame.

8. An implantable prosthetic valve comprising:

an annular frame comprising an inflow end and an outflow end and being radially collapsible and expandable between a radially collapsed configuration and a radially expanded configuration;

a leaflet structure positioned within the frame and secured thereto;

an outer skirt positioned around an outer surface of the frame, wherein the outer skirt has a lower edge secured to the frame and an upper edge stitched to the frame such that the outer skirt radially collapses around the outer surface of the frame when the frame is collapsed to the radially collapsed configuration and radially expands around the outer surface of the frame when the frame is expanded to the radially expanded configuration; and an annular sealing member positioned around and conforming to an outer surface of the outer skirt such that an inner surface of the sealing member lies flat against the outer surface of the outer skirt from an inflow end portion to an outflow end portion of the sealing member when the frame is in the radially expanded configuration, wherein the inflow end portion of the sealing member is located at the inflow end of the frame, and wherein the annular sealing member comprises a plurality of interconnected, angled projections that form an outermost radial surface of the annular sealing member that can contact and seal against native tissue.

9. The prosthetic valve of claim 8, wherein the sealing member comprises a sponge or foam material.

10. The prosthetic valve of claim 8, wherein the sealing member comprises a material that is configured to absorb blood and expand.

11. The prosthetic valve of claim 8, wherein the inflow end portion of the sealing member is disposed at an inflow end of the outer skirt that is disposed at the inflow end of the frame, and wherein the outflow end portion of the sealing member is disposed away from the inflow end and toward an outflow end of the outer skirt.

12. An implantable prosthetic valve comprising:

an annular frame comprising an inflow end and an outflow end and being radially collapsible and expandable between a radially collapsed configuration and a radially expanded configuration;

a leaflet structure positioned within the frame and secured thereto;

an outer skirt positioned around an outer surface of the frame, wherein the outer skirt has a lower edge secured to the frame and an upper edge secured to the frame via stitches such that the outer skirt radially collapses around the outer surface of the frame when the frame is collapsed to the radially collapsed configuration and radially expands around the outer surface of the frame when the frame is expanded to the radially expanded configuration; and a sealing member disposed on and projecting radially outward from an outer surface of the outer skirt, wherein the sealing member is made of a material that absorbs blood and does not overlap itself when the annular frame is in the radially collapsed configuration.

13. The prosthetic valve of claim 12, wherein the outer skirt comprises a first material and the sealing member comprises a second material, wherein the second material is different than the first material.

14. The prosthetic valve of claim 13, wherein the first material is a fabric.

15. The prosthetic valve of claim 14, wherein the second material comprises a material that is configured to absorb blood and expand.

16. The prosthetic valve of claim 12, wherein the sealing member extends completely around the outer skirt.

17. The prosthetic valve of claim 12, wherein the sealing member is stitched to the outer skirt.

18. The prosthetic valve of claim 12, wherein the sealing member has an upper end spaced axially from the upper edge of the outer skirt.

* * * * *